(12) United States Patent
Whelan et al.

(10) Patent No.: US 9,950,050 B2
(45) Date of Patent: Apr. 24, 2018

(54) VACCINES BASED ON HEPATITIS B CORE ANTIGENS

(71) Applicant: IQUR LIMITED, London (GB)

(72) Inventors: Michael Anthony Whelan, London (GB); Robert A. Field, Norwich (GB); David J. Rowlands, Leeds (GB)

(73) Assignee: IQUR LIMITED, London (GB)

( * ) Notice: Subject to any disclaimer, the term of this patent is extended or adjusted under 35 U.S.C. 154(b) by 0 days.

(21) Appl. No.: 15/119,367

(22) PCT Filed: Feb. 18, 2015

(86) PCT No.: PCT/GB2015/050460
§ 371 (c)(1),
(2) Date: Aug. 16, 2016

(87) PCT Pub. No.: WO2015/124919
PCT Pub. Date: Aug. 27, 2015

(65) Prior Publication Data
US 2017/0049871 A1 Feb. 23, 2017

(30) Foreign Application Priority Data
Feb. 18, 2014 (GB) .................................. 1402890.6

(51) Int. Cl.
| | | |
|---|---|---|
| *A61K 39/385* | (2006.01) | |
| *A61K 39/02* | (2006.01) | |
| *A61K 39/12* | (2006.01) | |
| *A61K 39/29* | (2006.01) | |
| *C12N 7/00* | (2006.01) | |
| *A61K 39/00* | (2006.01) | |

(52) U.S. Cl.
CPC .......... *A61K 39/0208* (2013.01); *A61K 39/12* (2013.01); *A61K 39/292* (2013.01); *A61K 39/385* (2013.01); *C12N 7/00* (2013.01); *A61K 2039/70* (2013.01); *C12N 2730/10134* (2013.01)

(58) Field of Classification Search
CPC .................................................. A61K 39/0208
See application file for complete search history.

(56) References Cited

U.S. PATENT DOCUMENTS

| | | |
|---|---|---|
| 7,270,821 B2 | 9/2007 | Gehin et al. |
| 8,128,938 B1 | 3/2012 | Luke et al. |
| 2004/0223965 A1 | 11/2004 | Gehin et al. |
| 2007/0286869 A1 | 12/2007 | Luke et al. |
| 2009/0227770 A1 | 9/2009 | Rappuoli et al. |
| 2012/0015899 A1 | 1/2012 | Lomonossoff et al. |

FOREIGN PATENT DOCUMENTS

| | | |
|---|---|---|
| EP | 0 421 635 A1 | 4/1991 |
| WO | 1999/040934 A1 | 8/1999 |
| WO | 2000/032625 A1 | 6/2000 |
| WO | 2001/077158 A1 | 10/2001 |
| WO | 2003/015815 A1 | 2/2003 |
| WO | 2004/053091 A2 | 6/2004 |
| WO | 2005/055957 A2 | 6/2005 |
| WO | 2011/048386 A1 | 4/2011 |
| WO | 2014/195713 A1 | 12/2014 |
| WO | 2016/087863 A1 | 6/2016 |
| WO | 2016/151337 A1 | 9/2016 |

OTHER PUBLICATIONS

International Search Report issued in connection with corresponding International Application No. PCT/GB2015/050460, dated Jun. 11, 2015, 5 pages.
Burtnick et al (2011). "The cluster 1 type VI secretion system is a major virulence determinant in *Burkholderia pseudomallei*" Infection and Immunity, 79(4) pp. 1512-1525.
Burtnick et al (2012). "Development of capsular polysaccharide-based glycoconjugates for immunization against melioidosis and glanders" Frontiers in Cellular and Infection Microbiology, vol. 2, pp. 1-10.
Harland D N et al (2007). "Identification of a LolC homologue in *Burkholderia pseudomallei*, a novel protective antigen for melioidosis" Infection and Immunity, vol. 75, No. 8, pp. 4173-4180.
Kratz et al (1999). "Native display of complete foreign protein domains on the surface of hepatitis B virus capsids" Proc. Natl. Acad. Sci. USA, vol. 96, pp. 1915-1920.
Nassal et al (2007). "A Structural Model for Duck Hepatitis B Virus Core Protein Derived by Extensive Mutagenesis" Journal of Virology, vol. 81(23) pp. 13218-13229.
Paoletti L C et al (2001). "Preclinical evaluation of group B *streptococcal* polysaccharide conjugate vaccines prepared with a modified diphtheria toxin and a recombinant duck hepatitis B core antigen" Vaccine Elsevier, vol. 20, No. 3-4, pp. 370-376.
Scott et al (2014). "*Burkholderia pseudomallei* Capsular polysaccharide Conjugates Provide Protection against Acute Melioidosis", Infection and Immunity, vol. 82, pp. 3206-3213.
Su et al (2010). "Immunization with the recombinant *Burkholderia pseudomallei* outer membrane protein Omp85 induces protective immunity in mice" Vaccine, 28(31) pp. 5005-5011.
Suwannasaen et al (2011). "Human immune responses to *Burkholderia pseudomallei* characterized by protein microarray analysis" Journal Infectious Diseases 203(7), pp. 1002-1011.
Tippayawat et al (2011). "*Burkholderia pseudomallei* proteins presented by monocyte-derived dendritic cells stimulate human memory T cells in vitro" Infection and Immunity, 79(1), pp. 305-313.
Yu et al (2013). "3.5A cryoEM Structure of Hepatitis B Virus Core Assembled from Full-Length Core Protein" PLOS ONE, vol. 8(9) pp. 1 to 11.

(Continued)

*Primary Examiner* — Albert M Navarro
(74) *Attorney, Agent, or Firm* — Kilpatrick Townsend & Stockton LLP

(57) ABSTRACT

The invention provides a protein comprising hepatitis B core antigen (HBcAg) with a sugar attached to an e1 loop. The protein may comprise a first and a second copy of HBcAg in tandem, wherein one or both copies of HBcAg has a sugar attached to the e1 loop. The first copy may have a sugar attached to the e1 loop and the second copy may comprise a peptide epitope in the e1 loop. The protein may be used to induce an immune response against the sugar and hence act as a vaccine.

28 Claims, 11 Drawing Sheets

(56) References Cited

OTHER PUBLICATIONS

Caldeira, Jerri C. And David S. Peabody, "Stability and assembly *in vitro* of bacteriophage PP7 virus-like Particles," *Journal of Nanobiotechnology* 2007, 5:10, 10 pages.

Janssens, Michiel Etienne et al., "Folding properties of the hepatitis B core as a carrier protein for vaccination research," *Amino Acids* (2010) 38:5, 1617-1626.

Peabody, David S., "Subunit Fusion Confers Tolerance to Peptide Insertions in a Virus Coat Protein," *Archives of Biochemistry and Biophysics* vol. 347, No. 1, Nov. 1, 1997, pp. 85-92.

Peabody, David S. et al., "Immunogenic Display of Diverse Peptides on Virus-like Particles of RNA Phage MS2," *J Mol Biol* (2008) 380, 252-263.

Peyret, Hadrien et al., "Tandem Fusion of Hepatitis B Core Antigen Allows Assembly of Virus-Like Particles in Bacteria and Plants with Enhanced Capacity to Accommodate Foreign Proteins," *PLOS ONE*, Apr. 1, 2015, 20 pages.

Peyret, Hadrien and George P. Lomonossoff, "The pEAQ vector series: the easy and quick way to produce recombinant proteins in plants," *Plant Mol Biol* (2013) 83:51-58.

Pumpens, Paul and Elmars Grens, "HBV Core Particles as a Carrier for B Cell/T Cell Epitopes," *Intervirology* 2001; 44:98-114.

Sainsbury, Frank et al., "pEAQ: versatile expression vectors for easy and quick transient expression of heterologous proteins in plants," *Plant Biotechnology Journal* (2009) 7, pp. 682-693.

Stahl, Stephen J. and Kenneth Murray, "Immunogenicity of peptide fusions to hepatitis B virus core antigen," *Proc Natl Acad Sci USA*, Aug. 1989, vol. 86, pp. 6283-6287.

Thermet A. et al., "Identification of Antigenic Regions of Duck Hepatitis B Virus Core Protein with Antibodies Elicited by DNA Immunization and Chronic Infection," *Journal of Virology*, Feb. 2004, vol. 78, No. 4, pp. 1945-1953.

Ulrich, Rainer et al., "Core Particles of Hepatitis B Virus as Carrier for Foreign Epitopes," *Advances in Virus Research*, 1998, vol. 50, pp. 141-182.

A 5 sec exposure

B

B 1 min exp

B

VACCINES BASED ON HEPATITIS B CORE ANTIGENS

CROSS-REFERENCE TO RELATED APPLICATIONS

This application is a national stage application under 35 U.S.C. § 371 of International Patent Application No. PCT/GB/050460, filed Feb. 18, 2015, which claims priority to Great Britain Application No. 1402890.6, filed Feb. 18, 2014.

FIELD OF THE INVENTION

The invention relates to proteins comprising hepatitis B core antigen (HBcAg) with a sugar attached to an e1 loop, processes for producing the proteins with the sugar attached, pharmaceutical compositions comprising the proteins and use of the proteins to induce an immune response in a subject.

BACKGROUND OF THE INVENTION

The Hepatitis B virus core (HBc) protein has a somewhat unique structure comprised of two anti-parallel α-helices which form a characteristic "spike" structure. Two HBc molecules then spontaneously dimerise to form a twin spike bundle. This bundle is the building block of a virus like particle (VLP). VLPs are attractive vaccine systems since their highly repetitious sequence delivers multiple copies of the antigen. Furthermore, the lack of viral nucleic acid makes them a particularly safe vector. HBc is particularly interesting as a vaccine carrier since it has several sites into which antigenic sequences may be inserted. The extreme immunogenicity of HBc is then also imparted to the inserted sequence, thus making that too immunogenic. The optimal insertion site is the Major Insertion Region (MIR). However, it was shown previously that when a large or hydrophobic sequence is inserted into the MIR, then monomeric HBc fails to dimerise and a VLP does not form. This resulted in a massive loss of immunogenicity.

Currently there is no licensed vaccine available for the bacterial biothreat agents *Burkholderia pseudomallei* and *Burkholderia mallei*, the causative agents of melioidosis and glanders respectively.

SUMMARY OF THE INVENTION

The invention is concerned with a vaccine delivery system based on the hepatitis B (HBV) core protein. A sugar is attached to the HBV core protein before delivery so that an immune response can be raised against the sugars.

The invention thus provides a protein comprising hepatitis B core antigen (HBcAg) with a sugar attached to an e1 loop. The protein may comprise a first and a second copy of HBcAg in tandem, wherein one or both copies of HBcAg has a sugar attached to the e1 loop.

The invention also provides:
a particle comprising multiple copies of a protein of the invention;
a process for producing a protein of the invention, which comprises attaching one or more sugars to the e1 loop;
a pharmaceutical composition comprising a protein of the invention or a particle of the invention and a pharmaceutically acceptable carrier or diluent;
a protein of the invention or a particle of the invention for use in a method of vaccination of the human or animal body;
use of a protein of the invention or a particle of the invention for the manufacture of a medicament for vaccination of the human or animal body; and
a method of inducing an immune response in a subject, which method comprises administering to the subject a protein of the invention or a particle of the invention.

BRIEF DESCRIPTION OF THE SEQUENCES

Figure 1:
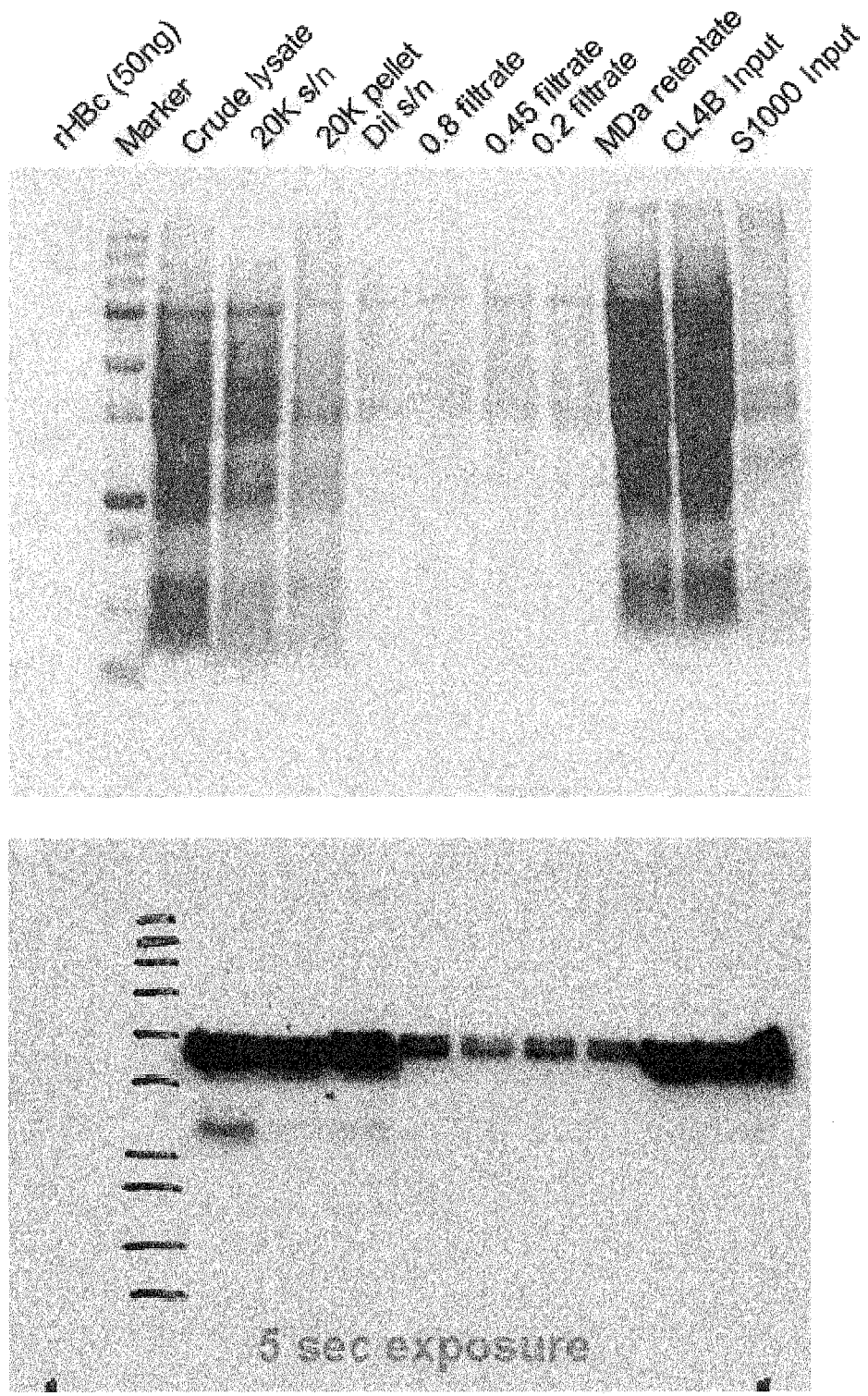
FIG. 1: SDS-PAGE confirmed that tandem cores were found in the soluble fraction of the yeast lysate. A crude lysate was taken (lane 3), spun at 20,000×g and the supernatant was taken (lane 4). Anything in the pellet (lane 5) was unusable. The supernatant was diluted (lane 6) and then passed through three filters of 0.8 µm, 0.45 µm and 0.2 µm (lanes 7-9). The material was passed over a cross-flow filter and the retentate kept (lane 10). This was filtered and then placed on a CL4B column (lane 11). The void volume was then passed over an S1000 column (lane 12).

SEQ ID NO: 1 is the 183 amino acid protein of the ayw subtype plus a 29 amino acid pre-sequence of HBcAg and the corresponding nucleotide sequence.

SEQ ID NO: 2 is the 183 amino acid protein of the ayw subtype plus a 29 amino acid pre-sequence of HBcAg.

SEQ ID NO: 3 is a sequence which HBcAg may comprise in order to balance the α-helices.

SEQ ID NO: 4 is the sequence of construct CoHo7e.

SEQ ID NO: 5 is the sequence of construct H3Ho.

SEQ ID NO: 6 is the sequence of the LolC-empty construct.

SEQ ID NO: 7 is the sequence of the LolC-K6 construct.

SEQ ID NO: 8 is the sequence of the LolC-K1 construct.

SEQ ID NO: 9 is a sequence of LolC.

DETAILED DESCRIPTION OF THE INVENTION

In addition, as used in this specification and the appended claims, the singular forms "a", "an", and "the" include plural referents unless the content clearly dictates otherwise. Thus, for example, reference to "a sugar" includes two or more such sugars, or reference to "a protein epitope" includes two or more such protein epitopes.

All publications, patents and patent applications cited herein, whether supra or infra, are hereby incorporated by reference in their entirety.

Hepatitis B Core Antigen (HBcAg)

HBcAg has 183 or 185 amino acids (aa) depending on the subtype of HBV. The sequence of the 183 amino acid protein of the ayw subtype plus a 29 amino acid pre-sequence is shown in SEQ ID NO: 2. The mature HBcAg runs from the Met residue at position 30 to the Cys residue at the extreme C-terminus, with the sequence from positions 1 to 29 being a pre-sequence.

The protein may comprise two copies of HBcAg forming a dimer. Dimers of HBcAg form the structural building blocks of VLPs. The HBcAg units are generally joined together in a head-to-toe fashion, i.e. the C-terminus of one unit is joined to the N-terminus of the adjacent unit. The units may be joined directly by a covalent bond (e.g. a peptide bond), but preferably they are joined by a linker which spaces the adjacent units apart and thereby prevents any problem with disruption of the packing of adjacent units. The nature of the linker is discussed below.

The HBcAg in the protein may be native full length HBcAg. The HBcAg has a sugar attached to the e1 loop. Where the protein comprises a first and a second copy of HBcAg in tandem, one copy of HBcAg has a sugar attached to the e1 loop. The other copy of HBcAg may be native HBcAg, may be a modified version of HBcAg as described herein, may have a sugar attached to the e1 loop or may comprise a protein epitope in the e1 loop. Examples of possible sugars and protein epitopes are discussed below.

As a general rule, any modifications are chosen so as not to interfere with the conformation of HBcAg and its ability to assemble into particles. Such modifications are made at sites in the protein which are not important for maintenance of its conformation, for example in the e1 loop, the C-terminus and/or the N-terminus. The e1 loop of HBcAg can tolerate insertions of e.g. from 1 to 500 amino acids without destroying the particle-forming ability of the protein.

The HBcAg sequence may be modified by substitution, insertion, deletion or extension. The size of insertion, deletion or extension may, for example, be from 1 to 500 aa, from 1 to 400 aa, from 1 to 300 aa, from 1 to 200 aa, from 3 to 100 aa or from 6 to 50 aa. Substitutions may involve a number of amino acids up to, for example, 1, 2, 5, 10, 20 or 50 amino acids over the length of the HBcAg sequence. An extension may be at the N- or C-terminus of HBcAg. A deletion may be at the N-terminus, C-terminus or at an internal site of the protein. Substitutions may be made at any position in the protein sequence. Insertions may also be made at any point in the protein sequence, but are typically made in surface-exposed regions of the protein such as the e1 loop. An inserted sequence may carry a protein epitope. One or more amino acids may be inserted so that one or more sugars can be subsequently attached. For example, 1, 2, 3, 4, 5, 6, 7, 8, 9, 10, 11 or 12 amino acids may be inserted. The amino acids may be inserted consecutively. Any amino acid inserted for the attachment of a sugar must be capable of having a sugar attached to it. Examples of such amino acids include lysine, arginine, asparagine, glutamine, aspartic acid or glutamic acid. For example, 1, 2, 3, 4, 5, 6, 7, 8, 9, 10, 11 or 12 lysines may be inserted. One or more alanines may be inserted either side of the one or more amino acids which have been inserted for the attachment of sugar. For example, 1, 2, 3, 4, 5, 6, 7, 8, 9, 10, 11, 12, 13, 14, 15, 16, 17, 18, 19 or 20 alanines may be inserted. The alanines may be inserted consecutively. More than one modification may be made to each HBcAg unit. Thus, it is possible to make a terminal extension or deletion and also an internal insertion. For example, a truncation may be made at the C-terminus and an insertion may be made in the e1 loop.

Each part of the HBcAg sequence in the protein of the invention preferably has at least 70% sequence identity to the corresponding sequence of a natural HBcAg protein, such as the protein having the sequence shown in SEQ ID NO: 2. More preferably, the identity is at least 80%, at least 90%, at least 97%, at least 98% or at least 99%. Methods of measuring protein homology are well known in the art and it will be understood by those of skill in the art that in the present context, homology is calculated on the basis of amino acid identity (sometimes referred to as "hard homology").

For example the UWGCG Package (Devereux et al (1984) Nucleic Acids Research 12: 387-395) provides the BESTFIT program which can be used to calculate homology (for example used on its default settings). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The e1 loop of HBcAg is at positions 68 to 90 of the mature sequence, and a protein epitope may be inserted anywhere between these positions. Amino acid for the attachment of a sugar as discussed above may be inserted anywhere between these positions. Preferably, the epitope or amino acid for the attachment of sugar is inserted in the region from positions 69 to 90, 71 to 90 or 75 to 85. Most preferred is to insert the epitope or the amino acid for the attachment of sugar between amino acid residues 79 and 80 or between residues 80 and 81. When a protein epitope or an amino acid for the attachment of sugar is inserted, the entire sequence of HBcAg may be maintained, or alternatively the whole or a part of the e1 loop sequence may be deleted and replaced by the protein sequence. Thus, amino acid residues 69 to 90, 71 to 90 or 75 to 85 may be replaced by a protein epitope or an amino acid for the attachment of sugar. Where a protein epitope or an amino acid for the attachment of sugar replaces e1 loop sequence, the replacement sequence is generally not shorter than the sequence that it replaces.

A C-terminal truncation of HBcAg will generally not go beyond aa 144 because if any further truncation is made particles may not form. Thus, the deleted amino acids may, for example, comprise aa 144 to the C-terminal aa (aa 183 or 185), aa 150 to the C-terminal aa, aa 164 to the C-terminal aa or aa 172 to the C-terminal aa. The C-terminus of HBcAg binds DNA, and truncation of the C-terminus therefore reduces or completely removes DNA from preparations of HBcAg and HBcAg hybrid proteins.

The protein of the invention forms particles which preferably resemble the particles formed by native HBcAg. The particle of the invention comprises multiple copies of the protein of the invention. The particle can be in the form of a VLP. The particles of the invention are typically at least 10 nm in diameter, for example from 10 to 50 nm or from 20 to 40 nm in diameter, but preferably they are about 27 nm in diameter (which is the size of native HBcAg particles). They comprise multiple HBcAg units, for example from 150 to 300 units, but generally they are fixed to about 180 or about 240 units (which are the numbers of units in native HBcAg particles). As the protein of the invention can be a dimer, this means that the number of protein monomers in the particles may be from 75 to 150 but is generally about 90 or about 120.

The linker between adjacent HBcAg copies is generally a chain of amino acids at least 1.5 nm (15 Å) in length, for example from 1.5 to 10 nm, from 1.5 to 5 nm or from 1.5 to 3 nm. It may, for example, comprise 4 to 40 aa or 10 to 30 aa, preferably 15 to 21 aa. The linker is generally flexible. The amino acids in the linker may, for example, include or be entirely composed of glycine, serine and/or proline. A preferred linker comprises one or more repeats of the sequence $Gly_n Ser$ ($G_n S$) where n is 2, 3, 4, 5, 6, 7 or 8. Alternatively, the linker may comprise one or more GlyPro (GP) dipeptide repeats. The number of repeats may, for example, be from 1 to 18, preferably from 3 to 12. In the case of $G_2 S$ repeats, the use of 5, 6 or 7 repeats has been found to allow the formation of particles. The linker may correspond to the hinge region of an antibody; this hinge region is thought to provide a flexible joint between the antigen-binding and tail domains of antibodies.

The two α-helices that comprise the HBc spike region are not symmetrical and so the resulting MIR does not point completely vertically from the VLP, but is slightly offset. Molecular modelling thus suggests that any antigen that was inserted may lie parallel to the VLP, rather than at right angles. This could possibly lead to steric hindrance and a decrease in immunogenicity. The HBcAg may comprise an inserted sequence which acts to "balance" the α-helices by adding an extra turn or turns to the first helix (which lies at positions 50 to 73 of the mature sequence). This results in the presentation of an inserted protein epitope in a perpendicular orientation to the VLP. This may be achieved by inserting from 3 to 12 amino acids (e.g. 3, 5 or 7 amino acids) into HBcAg. These amino acids are preferably uncharged amino acids such as alanine, leucine, serine and threonine. The inserted sequence is preferably AAALAAA (SEQ ID NO: 3). The insertion may be at a site between amino acids 50 and 75 of the mature sequence, for example at a site between residues 60 and 75 or residues 70 and 73.

Sugar

The term "sugar" refers to polysaccharides, oligosaccharides and monosaccharides. The protein comprises HBcAg with a sugar attached to an e1 loop. The protein may comprise a first and a second copy of HBcAg in tandem. Where there are two copies of HBcAg in tandem, one or both copies of HBcAg has a sugar attached to the e1 loop.

There may be more than one sugar attached to the e1 loop. The e1 loop may have more than one type of sugar attached. The e1 loop may have different sugars attached. Where there are two copies of HBcAg in tandem, there may be a different sugar or different sugars attached to the e1 loop in each HBcAg. It may be useful for simultaneously inducing an immune response to more than one pathogen or allergen if the sugars are derived from more than one pathogen or allergen. The sugar may be part of a glycoprotein so that the glycoprotein is attached to the e1 loop.

The sugar is attached to one or more amino acids in the e1 loop. The one or more amino acids for attachment of the sugar may be inserted into the e1 loop as described herein. The one or more amino acids for attachment of the sugar may be amino acids which occur naturally in HBcAg. Examples of such amino acids include lysine, arginine, asparagine, glutamine, aspartic acid or glutamic acid. The sugar may be attached to more than one naturally occurring amino acid. The sugar may be attached to a naturally occurring amino acid and an inserted amino acid.

The sugar may be derived from any pathogen or allergen. The sugar may comprise a T-cell or a B-cell epitope. If it is a T-cell epitope, it may be a cytotoxic T-lymphocyte (CTL) epitope or a T-helper (Th) cell epitope (e.g. a Th1 or Th2 epitope). There may be more than one epitope present. If there is more than one epitope present, one of the epitopes may be a T-helper cell epitope and another may be a B-cell or a CTL epitope. The presence of the T-helper cell epitope enhances the immune response against the B-cell or CTL epitope.

The choice of sugar depends on the disease that it is wished to raise an immune response or vaccinate against. The sugar may, for example, be from a pathogenic organism, a cancer-associated antigen or an allergen. The pathogenic organism may, for example, be a virus, a bacterium or a protozoan. The sugar may be from any of the sources described herein from which a protein epitope may be derived, such as pathogenic organisms and cancers, and which comprise a sugar.

Preferably, the pathogenic organism is derived from a bacterium. The bacterium may be *Burkholderia*, for example, *Burkholderia pseudomallei* or *Burkholderia mallei*. The pathogenic organism may comprise common capsule polysaccharide (CPS). The sugar may comprise antigen from CPS. The sugar may comprise one or more epitopes from CPS. CPS may be derived from *Burkholderia*, for example, *Burkholderia pseudomallei* or *Burkholderia mallei*. CPS comprises an unbranched homopolymer of 1-3 linked 2-O acetyl-6-deoxy-β-D-manno-heptopyranose. Therefore the sugar may comprise an unbranched homopolymer of 1-3 linked 2-O acetyl-6-deoxy-β-D-manno-heptopyranose. CPS has been identified as a major virulence determinant in both *B. pseudomallei* and *B. mallei* where loss of CPS expression in *B. pseudomallei* increases the MLD in mice from 70 cfu to greater than $10^6$ cfu. The CPS of *B. pseudomallei* has been demonstrated to provide partial protection against subsequent challenge in the mouse model, whilst passive transfer of antibodies raised against CPS can also provide protection.

Protein Epitope

The protein of the invention may comprise a first and a second copy of HBcAg in tandem, wherein the first copy has a sugar attached to the e1 loop and the second copy comprises a protein epitope in the e1 loop. The "first copy" may be either the N-terminal or C-terminal copy.

The protein epitope comprises a sequence of amino acids which raises an immune response. The epitope may be conformational or linear. It may be, for example, in a sequence of from 6 to 500 aa, 20 to 500 aa, 50 to 500 aa, 100 to 500 aa, 200 to 500 aa, 300 to 500 aa or 300 to 400 aa.

Large and/or hydrophobic insertions can be accommodated without VLP disruption. The protein epitope to be used as an insert may be of any suitable size that does not disrupt VLP formation. It is preferably less than 100 kDa, for example less than 80 kDa, less than 60 kDa, less than 40 kDa, less than 20 kDa, less than 10 kDa or less than 5 kDa. It may be more than 5 kDa, 10 kDa, 20 kDa, or 30 kDa.

The protein of the invention may contain more than one protein epitope, for example up to 2, 3, 5 or 8 protein epitopes. More than one copy of an epitope may be inserted in the copy of HBcAg; for example, from 2 to 8 copies may be inserted. Where there are two or more protein epitopes in the protein of the invention, they may be from the same or different organisms and from the same or different proteins.

The epitope may be a T-cell or a B-cell epitope. If it is a T-cell epitope, it may be a cytotoxic T-lymphocyte (CTL) epitope or a T-helper (Th) cell epitope (e.g. a Th1 or Th2 epitope). In a preferred embodiment of the invention, one of the epitopes is a T-helper cell epitope and another is a B-cell or a CTL epitope. The presence of the T-helper cell epitope enhances the immune response against the B-cell or CTL epitope.

The choice of epitope depends on the disease that it is wished to vaccinate against. The epitope may, for example, be from a pathogenic organism, a cancer-associated antigen or an allergen. The pathogenic organism may, for example, be a virus, a bacterium or a protozoan.

The epitope may be derived from any pathogen, such as but not limited to, a virus, including a member of the orthomyxoviridae (including for instance influenza A, B and C viruses), adenoviridae (including for instance a human adenovirus), Caliciviridae (such as Norwalk virus group), herpesviridae (including for instance HSV-1, HSV-2, EBV, CMV and VZV), papovaviridae (including for instance Human Papilloma Viruse—HPV), poxviridae (including for instance smallpox and vaccinia), parvoviridae (including for instance parvovirus B19), reoviridae (including for instance a rotavirus), coronaviridae (including for instance SARS), flaviviridae (including for instance yellow fever, West Nile virus, dengue, hepatitis C and tick-borne encephalitis), picornaviridae (including enteroviruses, polio, rhinovirus, and hepatitis A), togaviridae (including for instance rubella virus), filoviridae (including for instance Marburg and Ebola), paramyxoviridae (including, a parainfluenza virus, respiratory syncitial virus (RSV), mumps and measles), rhabdoviridae (including for instance rabies virus), bunyaviridae (including for instance Hanta virus), retroviridae (including for instance HIV and HTLV—Human T-cell Lymphoma virus) and hepadnaviridae (including for instance hepatitis B).

The epitope may be derived from bacteria, including *Burkholderia, M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneumococcus, Meningococcus, Hemophilus influenza* (type b), *Complybacteriosis, Moraxella catarrhalis, Donovanosis*, and *Actinomycosis*, fungal pathogens including *Candidiasis* and *Aspergillosis*, and parasitic pathogens including *Toxoplasma gondii, Taenia*, Flukes, Roundworms, Flatworms, *Amebiasis, Giardiasis, Cryptosporidium, Schitosoma, Pneumocystis carinii, Trichomoniasis* and *Trichinosis*.

The epitope may be derived from a pathogen that infects through a) the respiratory tract, b) the genito-urinary system or c) the gastrointestinal tract. Examples of such pathogens include a) members of the adenoviridae, paramyxoviridae and poxviridae, rhinovirus, influenza, and Hanta virus, b) *Ureaplasma urealyticum, Neisseria gonorrhoeae, Gardnerella vaginalis, Trichomonas vaginalis, Treponema pallidum, Chlamydia trachomatis, Haemophilus ducreyi*, herpes simplex virus, HPV, HIV, *Candida albicans, Treponema pallidum*, and *Calmatobacterium granulomatis*, and c) *Shigella, Salmonella, Vibrio Cholera, E. coli, Entamoeba histolytica, Campylobacter, Clostridium, Yersinia*, rotavirus, norovirus, adenovirus, astrovirus, Roundworms, Flatworms, *Giardiasis*, and *Cryptosporidium.*

The epitope to be used in the invention may be derived from a cancer such as, but not limited to, cancer of the lung, pancreas, bowel, colon, breast, uterus, cervix, ovary, testes, prostate, melanoma, Kaposi's sarcoma, a lymphoma (e.g. EBV-induced B-cell lymphoma) and a leukaemia. Specific examples of tumour associated antigens include, but are not limited to, cancer-testes antigens such as members of the MAGE family (MAGE 1, 2, 3 etc), NY-ESO-1 and SSX-2, differentiation antigens such as tyrosinase, gp100, PSA, Her-2 and CEA, mutated self antigens and viral tumour antigens such as E6 and/or E7 from oncogenic HPV types. Further examples of particular tumour antigens include MART-1, Melan-A, p97, beta-HCG, GaINAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSM (prostate mucin antigen), PSMA (prostate specific membrane antigen), prostate secretary protein, alpha-fetoprotein, CA125, CA19.9, TAG-72, BRCA-1 and BRCA-2 antigen.

Examples of other candidate epitopes for use in the invention include epitopes from the following antigens: the influenza antigens HA (hemagglutinin), NA (neuraminidase), NP (nucleoprotein/nucleocapsid protein), M1, M2, PB1, PB2, PA, NS1 and NS2; the HIV antigens gp 120, gp 160, gag, pol, Nef, Tat and Ref; the malaria antigens CS protein and Sporozoite surface protein 2; the herpes virus antigens EBV gp340, EBV gp85, HSV gB, HSV gD, HSV gH, HSV early protein product, cytomegalovirus gB, cytomegalovirus gH, and IE protein gP72; the human papilloma virus antigens E4, E6 and E7; the respiratory syncytial virus antigens F protein, G protein, and N protein; the pertactin antigen of *B. pertussis*; the tumor antigens carcinoma CEA, carcinoma associated mucin, carcinoma P53, melanoma MPG, melanoma P97, MAGE antigen, carcinoma Neu oncogene product, prostate specific antigen (PSA), prostate associated antigen, ras protein, and myc; and house dust mite allergen.

Preferably, the protein epitope is derived from *Burkholderia*, for example *Burkholderia pseudomallei* or *Burkholderia mallei*. The protein epitope may be derived from any of the proteins listed in Table 1. The protein epitope may comprise or consist of any of the proteins listed in Table 1. The protein epitope may be a fragment of any of the proteins listed in Table 1.

A LolC protein sequence described herein is:

```
                                                   (SEQ ID NO: 9)
ALGVAALIVVLSVMNGFQKEVRDRMLSVLAHVEIFSPTGSMPDWQLTA

KEARLNRSVIGAAPYVDAQALLTRQDAVSGVMLRGVEPSLEPQVSDIG

KDMKAGALTALAPGQFGIVLGNALAGNLGVGVGDKVTLVAPEGTITPA

GMMPRLKQFTVVGIFESGHYEYDSTLAMIDIQDAQALFRLPAPTGVRL

RLTDMQKAPQVARELAHTLSGDLYIRDWTQQNKTWFSAVQIEKRMMFI

ILTLIIAVAAFNLVSSLVMTVTNKQADIAILRTLGAQPGSIMKIFVVQ

GVTIGFVGTATGVALGCLIAWSIPWLIPMIEHAFGVQFLPPSVYFISE

LPSELVAGDVIKIGVIAGS
```

The sequence of the LolC protein may have homology with SEQ ID NO: 9 or any naturally occurring LolC protein, such

TABLE 1 proteins

| Protein | Comment |
|---|---|
| LolC (ABC transporter) | Efficacy in animal model.<br>Harland et al., "Identification of a LolC homologue in *Burkholderia pseudomallei*, a novel protective antigen for melioidosis." Infect Immun. 2007 Aug; 75(8): 4173-80. |
| PotF(ABC transporter) | Efficacy in animal model.<br>Harland et al., "Identification of a LolC homologue in *Burkholderia pseudomallei*, a novel protective antigen for melioidosis." Infect Immun. 2007 Aug; 75(8): 4173-80. |
| OppA(ABC transporter) | Human convalescent sera.<br>Suwannasaen et al., "Human immune responses to *Burkholderia pseudomallei* characterized by protein microarray analysis." J Infect Dis. 2011 Apr 1; 203(7): 1002-11.<br>Efficacy in animal model.<br>Harland et al., "Identification of a LolC homologue in *Burkholderia pseudomallei*, a novel protective antigen for melioidosis." Infect Immun. 2007 Aug; 75(8): 4173-80. |
| Tandem repeat sequence (Rp1) | Human sero-positive, healthy.<br>Tippayawat et al., "*Burkholderia pseudomallei* proteins presented by monocyte-derived dendritic cells stimulate human memory T cells in vitro." Infect Immun. 2011 Jan; 79(1): 305-13. |
| Tandem repeat sequence (Rp2) | Human sero-positive, healthy.<br>Tippayawat et al., "*Burkholderia pseudomallei* proteins presented by monocyte-derived dendritic cells stimulate human memory T cells in vitro." Infect Immun. 2011 Jan; 79(1): 305-13. |
| Omp85 (Outer membrane protein) | Efficacy in animal model.<br>Su et al., "Immunization with the recombinant *Burkholderia pseudomallei* outer membrane protein Omp85 induces protective immunity in mice." Vaccine. 2010 Jul 12; 28(31): 5005-11. |
| Hcp2 (type VI secretion protein) | Efficacy in animal model.<br>Burtnick et al., "The cluster 1 type VI secretion system is a major virulence determinant in *Burkholderia pseudomallei*." Infect Immun. 2011 Apr; 79(4): 1512-25. |

Preferably, the protein epitope is derived from LolC protein. The following paragraphs discuss LolC protein but the discussion applies equally to any of the proteins listed in Table 1. The LolC protein may be a naturally occurring LolC protein or may be a variant of a naturally occurring LolC protein. The protein epitope may comprise or consist of LolC protein. Therefore full length LolC or a fragment thereof may be inserted into the e1 loop.

as at least 60%, at least 70%, at least 80%, at least 90%, at least 95%, at least 97%, at least 98% or at least 99% identity, for example over the full sequence or over a region of at least 20, for example at least 50, at least 100, at least 150, at least 200, at least 250, at least 300, or at least 350 or more contiguous amino acids. Methods of measuring protein homology are well known in the art and are discussed above in relation to the HBV core protein.

The homologous protein typically differs from the naturally occurring LolC sequence by substitution, insertion or deletion, for example from 1, 2, 3, 4, 5 to 8 or more substitutions, deletions or insertions. The substitutions are preferably 'conservative' and may be made, for example, according to Table 2. Amino acids in the same block in the second column and preferably in the same line in the third column may be substituted for each other.

TABLE 2

| ALIPHATIC | Non-Polar | G A P |
| --- | --- | --- |
| | | I L V |
| | Polar-uncharged | C S T M |
| | | N Q |
| | Polar-charged | D E |
| | | K R |
| AROMATIC | | H F W Y |

A fragment of LolC protein to be used as an insert is a shortened version of a full length LolC protein that retains the ability of inducing an immune response. In some instances, a fragment may be at least 10%, such as at least 20%, at least 30%, at least 40% or at least 50%, preferably at least 60%, more preferably at least 70%, still more preferably at least 80%, even more preferably at least 90% and still more preferably at least 95% of the length of a naturally occurring LolC sequence or the sequence of SEQ ID NO: 9. For example a fragment may be from 6 to 354 aa, from 6 to 300 aa, from 6 to 200 aa, from 6 to 100 aa, from 6 to 50 aa or from 6 to 25 aa in length.

Process for Attaching the Sugar to the Protein

The invention provides a process for producing a protein of the invention. The process comprises attaching one or more sugars to the e1 loop. As described herein, sugar is attached to one or more amino acids in the e1 loop. The sugar may be attached by reductive amination of the oxidized sugar to an amino acid in the e1 loop. The amino acid may be lysine. Sodium periodate may be used to oxidise the sugar. Oxidising the sugar generates terminal aldehyde residues. Terminal aldehyde residues of the sugar can be reductively aminated to primary amines using sodium cyanoborohydride in PBS at pH 7.5. Before attaching the sugar, the protein can be purified.

The process may further comprise making the protein prior to the attachment of the sugar. The generation of the protein prior to the attachment of the sugar is described in more detail below.

Making the Protein Prior to Sugar Attachment

Prior to attaching the sugar, the protein may be made by recombinant DNA technology. The nucleic acid molecules may be made using known techniques for manipulating nucleic acids. Where the protein comprises two copies of HBcAg, typically, two separate DNA constructs encoding the two HBcAg copies are made and then joined together by overlapping PCR.

Prior to attaching the sugar, the protein may be produced by culturing a host cell containing a nucleic molecule encoding the protein under conditions in which the protein is expressed, and recovering the protein. Suitable host cells include bacteria such as *E. coli*, yeast, mammalian cells and other eukaryotic cells, for example insect Sf9 cells.

The vectors constituting nucleic acid molecules according to the invention may be, for example, plasmid or virus vectors. They may contain an origin of replication, a promoter for the expression of the sequence encoding the protein, a regulator of the promoter such as an enhancer, a transcription stop signal, a translation start signal and/or a translation stop signal. The vectors may also contain one or more selectable marker genes, for example an ampicillin resistance gene in the case of a bacterial plasmid or a neomycin resistance gene in the case of a mammalian vector. Vectors may be used in vitro, for example for the production of RNA or used to transform or transfect a host cell. The vector may also be adapted to be used in vivo, for example in a method of gene therapy or DNA vaccination.

Promoters, enhancers and other expression regulation signals may be selected to be compatible with the host cell for which the expression vector is designed. For example, prokaryotic promoters may be used, in particular those suitable for use in *E. coli* strains (such as *E. coli* HB101). A promoter whose activity is induced in response to a change in the surrounding environment, such as anaerobic conditions, may be used. Preferably an htrA or nirB promoter may be used. These promoters may be used in particular to express the protein in an attenuated bacterium, for example for use as a vaccine. When expression of the protein is carried out in mammalian cells, either in vitro or in vivo, mammalian promoters may be used. Tissue-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters and adenovirus promoters. All these promoters are readily available in the art.

The protein may be purified using conventional techniques for purifying proteins. The protein may, for example, be provided in purified, pure or isolated form. For use in a vaccine, the protein must generally be provided at a high level of purity, for example at a level at which it constitutes more than 80%, more than 90%, more than 95% or more than 98% of the protein in the preparation. However, it may be desirable to mix the protein with other proteins in the final vaccine formulation.

Inducing an Immune Response

A protein or particle of the invention can be used to induce an immune response. The protein or particle may be used as a vaccine. The protein or particle may be used to raise multiple simultaneous immune responses to all the components (the HBcAg and the sugar). Where the protein comprises two copies of HBcAg, the multiple immune responses may also include further immune responses against additional sugars and/or immune responses against the protein epitope. If all the sugars, and optional protein epitopes, are derived from the same source then this can induce an enhanced immune response against that source, for example a pathogen. If all the sugars, and optional protein epitopes, are derived from more than one source then this can induce simultaneous immune responses against the different sources, for example more than one pathogen.

The protein or particle may be employed alone or as part of a composition including, but not limited to, a pharmaceutical composition, a vaccine composition or an immunotherapeutic composition. The invention therefore provides a pharmaceutical composition (e.g. a vaccine composition) comprising a protein of the invention or a particle comprising multiple copies of the protein of the invention and a pharmaceutically acceptable carrier or diluent. The composition may further comprise an adjuvant. The composition can be used for vaccination of the human or animal body. The composition may be used to vaccinate against any of the pathogens described herein. In particular, the composition may be used to vaccinate against *Burkholderia*, for example, *Burkholderia pseudomallei* or *Burkholderia mallei*.

A protein of the invention or a particle of the invention can be used in a method of vaccination of the human or animal body. The invention provides use of a protein of the invention or a particle of the invention for the manufacture of a medicament for vaccination of the human or animal body. The protein or particle may be used to vaccinate against any of the pathogens described herein. In particular, the composition may be used to vaccinate against *Burkholderia*, for example, *Burkholderia pseudomallei* or *Burkholderia mallei*.

The principle behind vaccination is to induce an immune response in a host so as to generate an immunological memory in the host. This means that, when the host is exposed to the virulent pathogen, it mounts an effective (protective) immune response, i.e. an immune response which inactivates and/or kills the pathogen. The invention forms the basis of a vaccine against any of the pathogens described herein, for example *Burkholderia*. The protein could simultaneously vaccinate an individual to any of a wide range of diseases and conditions depending on the sugar and optional protein epitope which the protein comprises. Such diseases and conditions include any of those described herein and HBV, HAV, HCV, foot-and-mouth disease, polio, herpes, rabies, AIDS, dengue fever, yellow fever, malaria, tuberculosis, whooping cough, typhoid, food poisoning, diarrhoea, meningitis and gonorrhoea. The sugars and protein epitopes are chosen so as to be appropriate for the disease against which the vaccine is intended to provide protection.

The invention provides a method of inducing an immune response in a subject comprising administering to the subject the protein or particle of the invention. Preferably the immune response is against *Burkholderia*, for example, *Burkholderia pseudomallei* or *Burkholderia mallei*.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs as well as pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

In some instances, the invention may be administered to any suitable subject and in particular any suitable subject of a given species, preferably a suitable human subject. Thus, as many subjects as possible may, for instance, be subject to administration without emphasis on any particular group of subjects. For instance, a population of subjects as a whole, or as many as possible, may be subject to administration.

The protein or particle of the invention is for administration to a subject. It may be administered simultaneously or sequentially with an adjuvant. Therefore the composition of the invention comprising the protein or particle may also comprise an adjuvant. The composition of the invention may be one which is to be delivered by injection (such as intradermal, subcutaneous, intramuscular, intravenous, intraosseous, and intraperitoneal), transdermal particle delivery, inhalation, topically, orally or transmucosally (such as nasal, sublingual, vaginal or rectal).

The compositions may be formulated as conventional pharmaceutical preparations. This can be done using standard pharmaceutical formulation chemistries and methodologies, which are available to those skilled in the art. For example, compositions containing the protein or particle with or without an adjuvant can be combined with one or more pharmaceutically acceptable excipients or vehicles to provide a liquid preparation. Thus also provided is a pharmaceutical composition comprising the protein or particle together with a pharmaceutically acceptable carrier or diluent. The composition optionally comprises an adjuvant.

Auxiliary substances, such as wetting or emulsifying agents, pH buffering substances and the like, may be present. These carriers, diluents and auxiliary substances are generally pharmaceutical agents which may be administered without undue toxicity and which, in the case of antigenic compositions will not in themselves induce an immune response in the individual receiving the composition. Pharmaceutically acceptable carriers include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable carrier that serves as a stabilizer, particularly for peptide, protein or other like molecules if they are to be included in the composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

Alternatively, the protein or particle and/or the adjuvant may be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

Once formulated the compositions can be delivered to a subject in vivo using a variety of known routes and techniques. For example, the liquid preparations can be provided as an injectable solution, suspension or emulsion and administered via parenteral, subcutaneous, intradermal, intramuscular, intravenous intraosseous and intraperitoneal injection using a conventional needle and syringe, or using a liquid jet injection system. Liquid preparations can also be administered topically to skin or mucosal tissue (e.g. nasal, sublingual, vaginal or rectal), or provided as a finely divided spray suitable for respiratory or pulmonary administration. Other modes of administration include oral administration, suppositories, and active or passive transdermal delivery techniques.

Typically, the protein or particle of the invention is administered to a subject in an amount that will be effective in modulating an immune response. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed. A prophylactically effective amount is an amount which prevents the onset of one or more symptoms of the disease or disorder.

Typically, the protein or particles are administered in a dose of from 0.1 to 200 mg, preferably from 1 to 100 mg, more preferably from 10 to 50 mg body weight. The vaccine may be given in a single dose schedule or a multiple dose schedule, for example in from 2 to 32 or from 4 to 16 doses. The routes of administration and doses given above are intended only as a guide, and the route and dose may ultimately be at the discretion of the physician.

In some cases after an initial administration a subsequent administration of the composition of the invention may be performed. In particular, following an initial administration a subject may be given a "booster". The booster may be, for instance, a dose chosen from any of those mentioned herein. The booster administration may, for instance, be at least a week, two weeks, four weeks, six weeks, a month, two months or six months after the initial administration.

The protein or particle of the invention and an adjuvant may be administered sequentially or simultaneously, preferably simultaneously. The two entities may be administered in the same or different compositions, preferably the same composition. An adjuvant is delivered so that an adjuvant effect is seen, that is the immune response seen will differ from that if the adjuvant had not been administered with the antigen. The two entities may be administered at the same or different sites, preferably the same sites. Preferably, the two entities are administered in the same composition at the same site at the same time preferably via injection.

Any suitable adjuvant may be used. Currently used vaccine adjuvants include:

Inorganic compounds, such as aluminium salts (e.g. aluminium hydroxide and aluminium phosphate) or calcium phosphate. Aluminium salts are otherwise known as alum.

Oil emulsions and surfactant based formulations, e.g. MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion).

Particulate adjuvants, e.g. virosomes (unilamellar liposomal vehicles incorporating e.g. influenza hemagglutinin), AS04 ([SBAS4] Al salt with MPL), ISCOMS (structured complex of saponins and lipids), and polylactide co-glycolide (PLG).

Microbial derivatives (natural and synthetic), e.g. monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), and modified LT and CT (genetically modified bacterial toxins to provide non-toxic adjuvant effects).

Endogenous human immunomodulators, e.g. hGM-CSF or hIL-12 (cytokines that can be administered either as protein or plasmid encoded), and Immudaptin (C3d tandem array).

Inert vehicles, such as gold particles.

Preferably the adjuvant used is alum. Most preferably the adjuvant is a mixture of aluminium hydroxide and magnesium hydroxide, for example Inject alum (Pierce Laboratories).

The invention is illustrated by the following Example:

EXAMPLE

Materials & Methods
Design of Constructs

All tandem core clones are derived from the parental construct CoHo7e. In this version of tandem core, α-helices are "balanced" as described above, and both copies of HBc have the nucleic acid binding region removed. Thus, the construct is designated a homo-tandem since both versions of core are essentially identical, the only differences being silent mutations to allow for altered restriction sites. The sequence of tandem core CoHo7e used was:

```
                                          (SEQ ID NO: 4)
MDIDPYKEFGATVELLSFLPSDFFPSVRDLLDTASALYREALESPEHC

SPHHTALRQAILCWGELMTLATWVGNNLEGSAGGGRDPASRDLVVNYV

NTNMGLKIRQLLWFHISCLTFGRETVLEYLVSFGVWIRTPPAYRPPNA

PILSTLPETTVVGGSSGGSGGSGGSGGSGGSGGSTMDIDPYKEFGATV

ELLSFLPSDFFPSVRDLLDTASALYREALESPEHCSPHHTALRQAILC

WGELMTLATWVGNNLEFAGASDPASRDLVVNYVNTNMGLKIRQLLWFH

ISCLTFGRETVLEYLVSFGVWIRTPPAYRPPNAPILSTLPETTVVL
```

The H3Ho construct was based on the original CoHo version of tandem core, as outlined in international application WO 2001/077158. A hexa-lysine insert was designed which would produce "hotspots" of reactivity onto which CPS could be bound using standard amine chemistry. These were designed synthetically and included a redesigned MIR which included the sequence AAALAAA (SEQ ID NO: 3) to "balance" the α-helices as described above. The synthetic inserts were ligated to produce H3Ho. The final sequences was verified and was as follows:

```
                                          (SEQ ID NO: 5)
MSDIDPYKEFGATVELLSFLPSDFFPSVRDLLDTASALYREALESPEH

CSPHHTALRQAILCWGELMTLATWVAAALAAAEGSDPASRDLVVNYVN

TNMGLKIRQLLWFHISCLTFGRETVLEYLVSFGVWIRTPPAYRPPNAP

ILSTLPETTVVGGSSGGSGGSGGSGGSTMDIDPYKEFGATVELLSFLP

SDFFPSVRDLLDTASALYREALESPEHCSPHHTALRQAILCWGELMTL

ATWVAAALAAAESGDPASRDLVVNYVNTNMGLKIRQLLWFHISCLTFG

RETVLEYLVSFGVWIRTPPAYRPPNAPILSTLPETTVVLE
```

An alternative approach was to insert a protein antigen isolated from *Burkholderia*. The LolC protein has been shown previously to be immunogenic and so was chosen as a potential insert. However, in order to ensure that assembly of the VLP was not impeded, regions of α-helical folding were found at both the N and C termini. Thus, insertion of the antigen would be from an α-helical secondary structure into the α-helix of the HBc spike. Currently, there is no crystallographic data for LolC so the structure was predicted using the PSIPRED algorithm (http://bioinf.cs.ucl.ac.uk/psipred/). The predicted insertion and flanking regions were synthesised chemically and inserted into core 1 of H3Ho using standard ligation techniques. Final sequencing confirmed that this had been successful. LolC-empty sequence:

(SEQ ID NO: 6)
MDIDPYKEFGATVELLSFLPSDFFPSVRDLLDTASALYREALESPEHC

SPHHTALRQAILCWGELMTLATWVAAALAAAEGSALGVAALIVVLSVM

NGFQKEVRDRMLSVLAHVEIFSPTGSMPDWQLTAKEARLNRSVIGAAP

YVDAQALLTRQDAVSGVMLRGVEPSLEPQVSDIGKDMKAGALTALAPG

QFGIVLGNALAGNLGVGVGDKVTLVAPEGTITPAGMMPRLKQFTVVGI

FESGHYEYDSTLAMIDIQDAQALFRLPAPTGVRLRLTDMQKAPQVARE

LAHTLSGDLYIRDWTQQNKTWFSAVQIEKRMMFIILTLIIAVAAFNLV

SSLVMTVTNKQADIAILRTLGAQPGSIMKIFVVQGVTIGFVGTATGVA

LGCLIAWSIPWLIPMIEHAFGVQFLPPSVYFISELPSELVAGDVIKIG

VIAGSDPASRDLVVNYVNTNMGLKIRQLLWFHISCLTFGRETVLEYLV

SFGVWIRTPPAYRPPNAPILSTLPETTVVGGSSGGSGGSGGSGGSTMD

IDPYKEFGATVELLSFLPSDFFPSVRDLLDTASALYREALESPEHCSP

HHTALRQAILCWGELMTLATWVAAALAAAESGDPASRDLVVNYVNTNM

GLKIRQLLWFHISCLTFGRETVLEYLVSFGVWIRTPPAYRPPNAPILS

TLPETTVVLE

Two variations of the LolC insertion were then made by cleaving core 2 of the H3Ho LolC-empty construct using PstI and XhoI. Synthetic inserts containing either hexalysine or a single lysine flanked by repeating alanine residues were then ligated in. Again, sequencing confirmed their identity. LolC-K6 sequence:

(SEQ ID NO: 7)
MDIDPYKEFGATVELLSFLPSDFFPSVRDLLDTASALYREALESPEHC

SPHHTALRQAILCWGELMTLATWVAAALAAAEGSALGVAALIVVLSVM

NGFQKEVRDRMLSVLAHVEIFSPTGSMPDWQLTAKEARLNRSVIGAAP

YVDAQALLTRQDAVSGVMLRGVEPSLEPQVSDIGKDMKAGALTALAPG

QFGIVLGNALAGNLGVGVGDKVTLVAPEGTITPAGMMPRLKQFTVVGI

FESGHYEYDSTLAMIDIQDAQALFRLPAPTGVRLRLTDMQKAPQVARE

LAHTLSGDLYIRDWTQQNKTWFSAVQIEKRMMFIILTLIIAVAAFNLV

SSLVMTVTNKQADIAILRTLGAQPGSIMKIFVVQGVTIGFVGTATGVA

LGCLIAWSIPWLIPMIEHAFGVQFLPPSVYFISELPSELVAGDVIKIG

VIAGSDPASRDLVVNYVNTNMGLKIRQLLWFHISCLTFGRETVLEYLV

SFGVWIRTPPAYRPPNAPILSTLPETTVVGGSSGGSGGSGGSGGSTMD

IDPYKEFGATVELLSFLPSDFFPSVRDLLDTASALYREALESPEHCSP

HHTALRQAILCWGELMTLATWVAAALAAAESGGSGSKKKKKKGSGSSG

DPASRDLVVNYVNTNMGLKIRQLLWFHISCLTFGRETVLEYLVSFGVW

IRTPPAYRPPNAPILSTLPETTVVLE

LolC-K1 Sequence:

(SEQ ID NO: 8)
MDIDPYKEFGATVELLSFLPSDFFPSVRDLLDTASALYREALESPEHC

SPHHTALRQAILCWGELMTLATWVAAALAAAEGSALGVAALIVVLSVM

NGFQKEVRDRMLSVLAHVEIFSPTGSMPDWQLTAKEARLNRSVIGAAP

YVDAQALLTRQDAVSGVMLRGVEPSLEPQVSDIGKDMKAGALTALAPG

QFGIVLGNALAGNLGVGVGDKVTLVAPEGTITPAGMMPRLKQFTVVGI

FESGHYEYDSTLAMIDIQDAQALFRLPAPTGVRLRLTDMQKAPQVARE

LAHTLSGDLYIRDWTQQNKTWFSAVQIEKRMMFIILTLIIAVAAFNLV

SSLVMTVTNKQADIAILRTLGAQPGSIMKIFVVQGVTIGFVGTATGVA

LGCLIAWSIPWLIPMIEHAFGVQFLPPSVYFISELPSELVAGDVIKIG

VIAGSDPASRDLVVNYVNTNMGLKIRQLLWFHISCLTFGRETVLEYLV

SFGVWIRTPPAYRPPNAPILSTLPETTVVGGSSGGSGGSGGSGGSTMD

IDPYKEFGATVELLSFLPSDFFPSVRDLLDTASALYREALESPEHCSP

HHTALRQAILCWGELMTLATWVAAALAAAESGGSGSGGGKGGGSGSSG

DPASRDLVVNYVNTNMGLKIRQLLWFHISCLTFGRETVLEYLVSFGVW

IRTPPAYRPPNAPILSTLPETTVVLE

Design of Plasmids

Protein expression was carried out using two systems; the yeast *Pichia* pastoris and a *baculovirus* vector. This required the use of two different plasmids, specifically, pPICz (Invitrogen) for yeast and pOET1 (Oxford Expression Technologies) for *baculovirus*. The H3Ho sequence was inserted into the multi-cloning site of pPICz using MfeI and pspOMI, whereas pOET1 was inserted using pspOMI and BclI.

Protein Expression of Tandem Core in Yeast

Yeast were transformed by electroporation with 300 ng of linearised plasmid DNA. The yeast were then streaked onto YPD plates containing 100 μg/ml Zeocin and the largest clones selected. These clones were then individually challenged with increasing concentrations of Zeocin and the most resistant clone selected to be transformed a second time by electroporation. The process was repeated using selection plates with higher levels of Zeocin for clone selection. In this way, high copy-number clones were developed which had vastly improved VLP expression levels. Large scale yeast cultures were set up in 200 mls of YPD. After approximately 4 days, the media was replaced with induction media and the yeast induced using methanol (0.8% for 72 hrs). After this time period, the yeast cells were harvested by centrifugation at 1500 g and the pellets stored at −80° C. before purification.

Protein Expression of Tandem Core in *Baculovirus*

Recombinant virus was produced by co-transfection in Sf9 insect cells. Duplicate reaction mixtures, each containing flashBACPRIME viral DNA (100 ng) and transfer vector DNA (500 ng; pOET1-K6-lolc) together with Lipofectin liposome forming reagent (baculoFECTIN), were added to 35 mm$^2$ dishes with SD insect cells seeded at a density of $1 \times 10^6$ cells/dish. The dishes were then incubated at 28° C. for 5 days, following which the medium containing each virus was harvested into sterile tubes. A stock of virus was created from 50 ml of Sf9 cells, at a density of $2 \times 10^6$ cells/ml, infected with 0.5 ml of the co-transfection mix. The infected shake culture was incubated for 5 days at 28° C. and then harvested by centrifugation at 500×g for 20 min at 4°

C. For expression of protein, Sf9 cells were seeded in 35 mm² dishes at 1×10⁶ cells/dish, whereas Tni cells were seeded at 0.5×10⁶ cells/dish. Each dish was infected with the virus at moi 5. Following 72 hrs incubation at 28° C. the cell pellets and supernatants were harvested from each dish.

Purification of Protein Regardless of the expression vector used, or the nature of the insert, purification was carried out in a similar manner. Induced cells were harvested and spun down (300×g) before being resuspended in lysis buffer (20 mM Tris pH 8.4, 5 mM EDTA, 5 mM DTT, 2 mM AEBSF) at a ratio of 2.5 g wet weight/10 mls lysis buffer. The resulting solution was then passed through a microniser (AVP Gaulin LAB 40) set at 500 psi three times. Detergent (Triton X100) was added to make a 0.5% solution and the lysate spun for 30 mins (25,000×g) before harvesting the supernatant. The clarified supernatant was passed through a 0.8 um dead end filter (Nalgene), followed by a 0.45 um and finally a 0.2 um filtration. This material was diluted ten-fold (20 mM Tris pH 8.4, 5 mM EDTA) before being passed over a tangential flow device with a 1 MDa molecular weight cut-off (Pellicon). This step both removed low molecular weight contaminants and reduced volume down to 25 mls.

The concentrated lysate was then applied to an XK26/92 column packed with Sepharose CL4B resin driven by an Akta Pure FPLC system. The buffer was 20 mM Tris pH 8.4, 5 mM EDTA. The fractions were monitored at 260, 280 and 350 nm. The void volume was collected since this contains large proteins including VLP. The remainder of protein isolated over the column was discarded. The void volume fractions were pooled and concentrated using tangential flow (Pellicon) back down to 10 mls. This material was then passed over an XK26/55 column packed with Sephacryl S1000 resin. This resin has a much larger pore size and is capable of resolving VLP from other large proteins. Previously, we had calibrated the column using recombinant monomeric HBc (Biospacific Inc) and therefore knew when assembled VLP would elute. These fractions were collected and concentrated over tangential flow a final time.

Identity and Qualification of Protein

Samples were routinely stored at each step of the purification process, thus allowing in-process monitoring. It was known that whilst each expression system undoubtedly made VLP, not all tandem core proteins achieved this final conformation. Therefore, the most important contaminant that needed to be removed was actually tandem core itself in either the monomeric or misfolded state. However, SDS-PAGE and western blotting are, by definition, denaturing techniques so these had to be coupled with knowledge of protein size which could be estimated using the retention time on the FPLC columns.

Samples containing tandem core were characterised by electrophoresis at all stages of the process on 12.5% SDS-polyacrylamide gels (Laemmli, 1970) followed by Coomassie blue staining. Western Blot analyses were performed as described (Konig, et al., 1998) using a monoclonal primary antibody against HBc protein (10E11[Abcam]) followed by a mouse secondary antibody conjugated to horseradish peroxidase and the chemiluminescent substrate ECL-plus (Amersham Pharmacia). Protein concentrations were measured by the Bradford method (BioRad).

Electron Microscopy

All samples were diluted to 0.1 mg/ml in 20 mM Tris HCl pH 8 and sonicated in a water bath sonicator for 45 seconds immediately prior to adsorption to grids. Formvar/carbon coated copper grids (400 mesh) were placed carbon side down on droplets of the diluted samples on parafilm. Material was allowed to adsorb for 10 min. Grids were then washed in 4 changes of 1% uranyl acetate. The grid was incubated for 20 seconds with the final change of uranyl acetate prior to blotting and air drying. Grids were viewed and digitally imaged on a FEI Tecnai G2 TEM. Images were taken at a magnification of 87,000×, 43,000× and 26,000×.

ELISA for Antigenicity of LolC

A 96-well microtiter plate was coated for 24 hours at 4° C. with 100 μL/well of purified LolC (standard, 2-0.03 μg/mL), VLPs (negative control, 30-0.2 μg/mL) and VLP-LolC (test sample, 30-0.2 m/mL). All samples were serially diluted two-fold in phosphate-buffered saline (1× Dulbecco's PBS, Invitrogen). Each well was washed three times with PBS-0.05% Tween 20, and blocked with 200 μL of PBS containing 5% (w/v) skimmed milk powder for 1 hour at 37° C. Each well was then washed three times with PBS-0.05% Tween 20 and a 1:1000 dilution of sera from mice vaccinated with endotoxin-free LolC protein added (100 μL/well) and incubated for 1 hour at 37° C. Following three washes in PBS-Tween 20, a 1:2000 dilution of IgG goat anti-mouse horseradish peroxidase conjugate was added to each well (100 μL) and incubated for 1 hour at 37° C. Each well was washed a further six times in PBS-Tween 20 and bound conjugate detected with ABTS/hydrogen peroxide substrate (100 μL/well) with incubation at room temperature for 20 minutes prior to optical density measurement at 414 nm.

Chemical Conjugation of CPS to VLP

Sodium meta-periodate (6 mg, 0.3 mmol) and CPS (5 mg) were dissolved in PBS (1 ml) and the reaction mixture was left at room temperature for 1 hour. Excess sodium meta-periodate was removed using a PD-10 desalting column (GE Healthcare) equilibrated with PBS. The oxidized CPS was added to a solution of protein at 5 mg/ml (1 ml) in PBS. 20 μl of NaBH₃CN [1 M in 10 mMNaOH] was added to the solution and it was left for four days at room temperature in the dark. 20 μl of NaBH₄ [1M NaBH₄ in 10 mMNaOH] was added, after agitation the reaction was left for 40 min. The solution was diluted in MQ-H₂O and extensively dialyzed against ammonium bicarbonate buffer [20 mM, pH 7.8] and concentrated in vacuousing speed-vac (Thermo Scientific).

The concentrated protein sample was purified on an AKTA Xpress FPLC purification system. The conjugate solution was injected onto an S500 sepharose SEC column XK 26/60 (GE Healthcare) and eluted using ammonium bicarbonate buffer (20 mM, pH 7.8) at 1 ml/min. All fractions (2.5 ml) were collected and analysed for carbohydrate using the phenol:sulphuric acid assay and by TEM and dot-blot analysis. The pooled fractions were concentrated in vacuo (speed-vac, Thermo Scientific) and dialyzed into PBS.

Results

Protein Isolation from Yeast Samples

Samples were taken throughout the process and thus it was possible to track the purity enrichment as the process proceeded. Most importantly, regardless of the insert present, the majority of tandem core was found in the soluble fraction after the initial centrifugation post-lysis. Only a minority of core protein was found in the pellet from this spin which suggests that chimeric VLP remain soluble despite their complex composition.

The isolation of VLP from either yeast or *Baculovirus* lysates is somewhat unusual since it has been found that affinity chromatography is not readily compatible with tandem core. Hence, the method that evolved was based on gradual refinements of size class within the sample. Initially, very large debris was removed by filtration, leaving particles less than 200 nm and below present. The samples were then passed over a tangential flow filter with 1 MDa molecular weight cut-off. This served to retain the large VLPs but removed some of the low molecular weight contaminants.

The samples were then separated using CL4B size exclusion chromatography (SEC). This matrix has a relatively small pore size and very large material, including VLPs, will not enter the resin. Thus, large material passes directly through the column and is found in the void volume. However, a considerable amount of small proteins do enter the resin and are retarded. Therefore, by retaining only the void volume the samples are effectively enriched. SDS-PAGE and western blot once again shows that the majority of tandem core is, indeed, found in the CL4B void volume.

The CL4B void sample was then passed over an S1000 SEC column. This is conventionally used to isolate large molecules such as nucleic acids, but also is capable of resolving VLP from other large debris. The column had previously been calibrated using recombinant HBc which were known to be VLP of a similar size to tandem core VLP (34.6 nm). Thus, it was possible to determine that tandem core VLP should be found in the final ⅓ of the column elution. This was, indeed, the case and pure VLP were isolated from these fractions. This was confirmed by electron microscopy.

Figure 2:
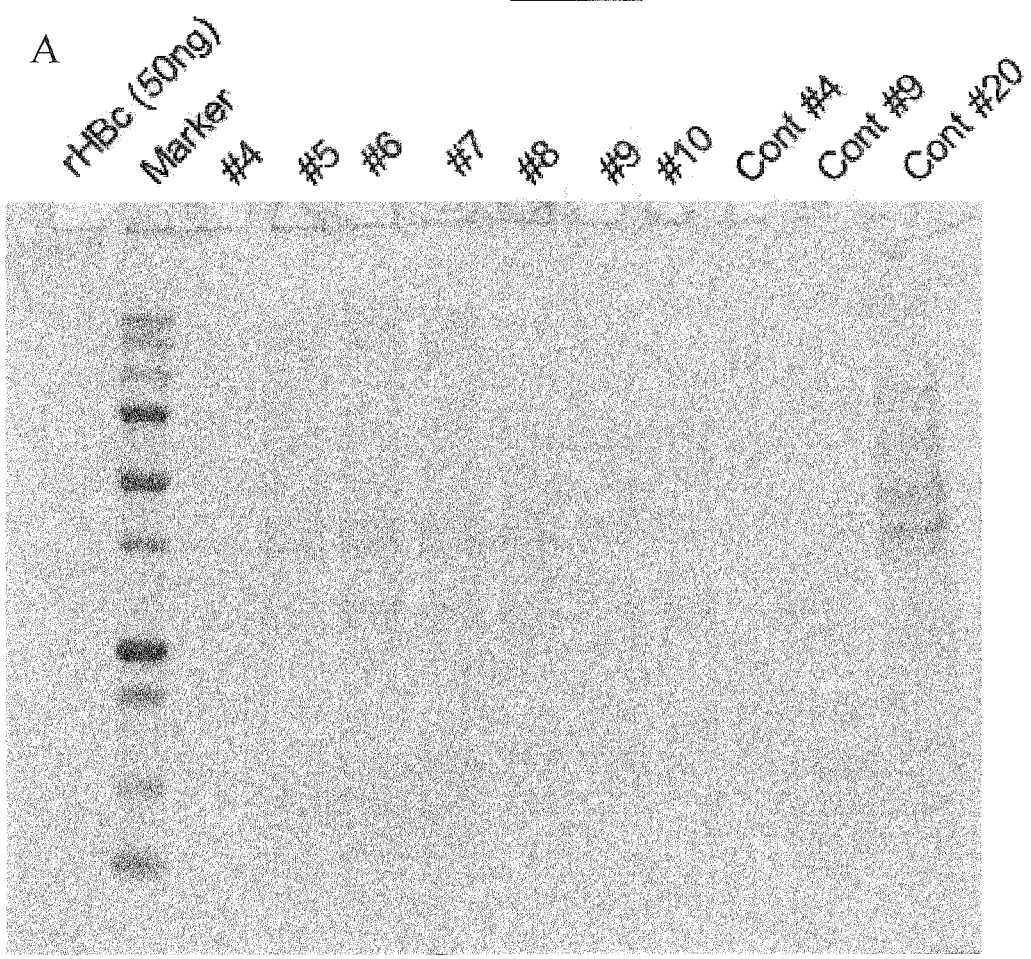
FIG. 2: VLP were isolated from the void volume of the CL4B column (large peak on left panel of (B)). The numbers above the lanes are fraction numbers collected from the CL4B column.
Figure 2:
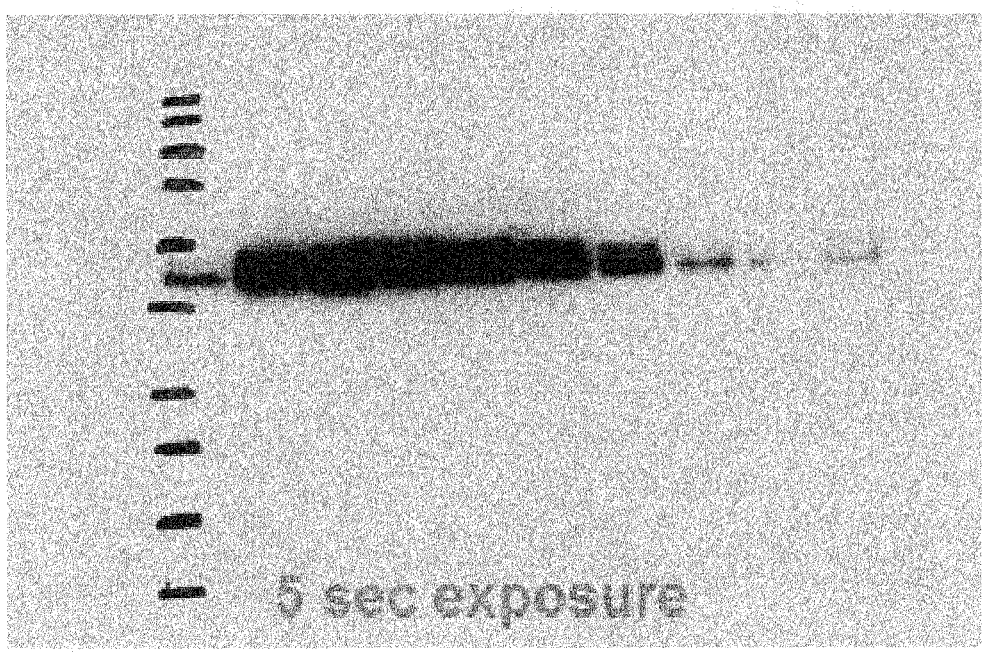
Figure 2:
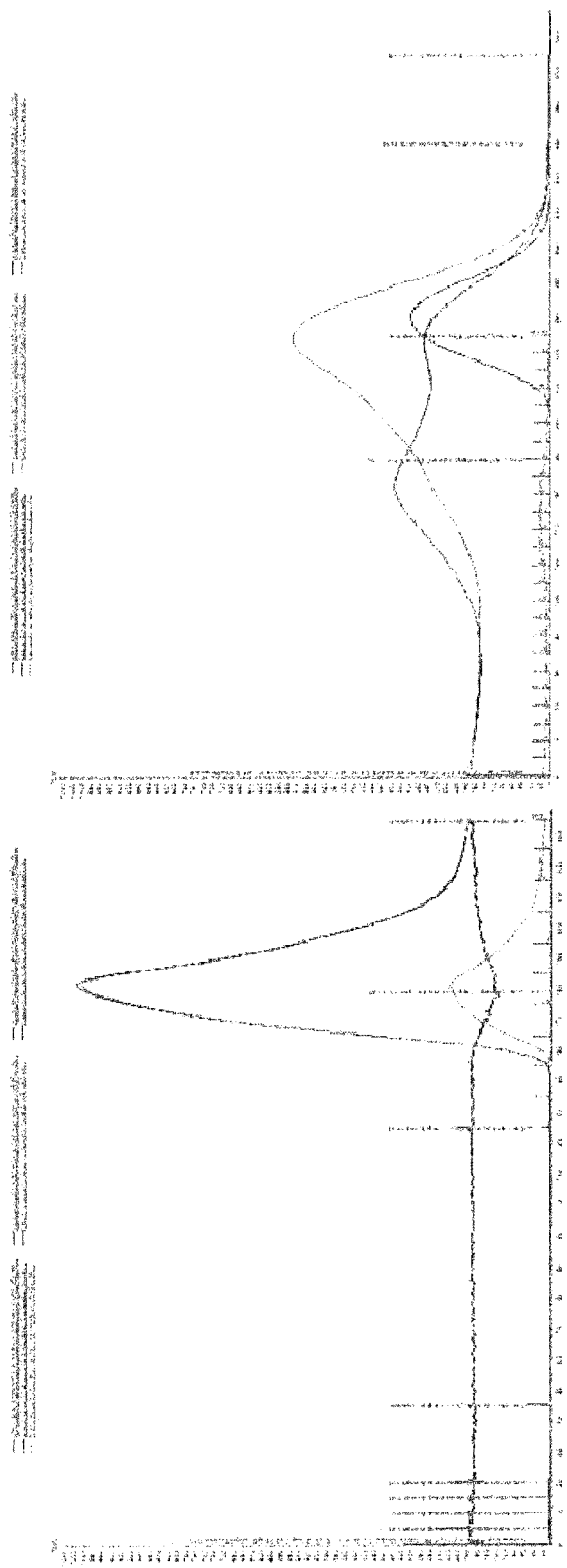
Figure 3:
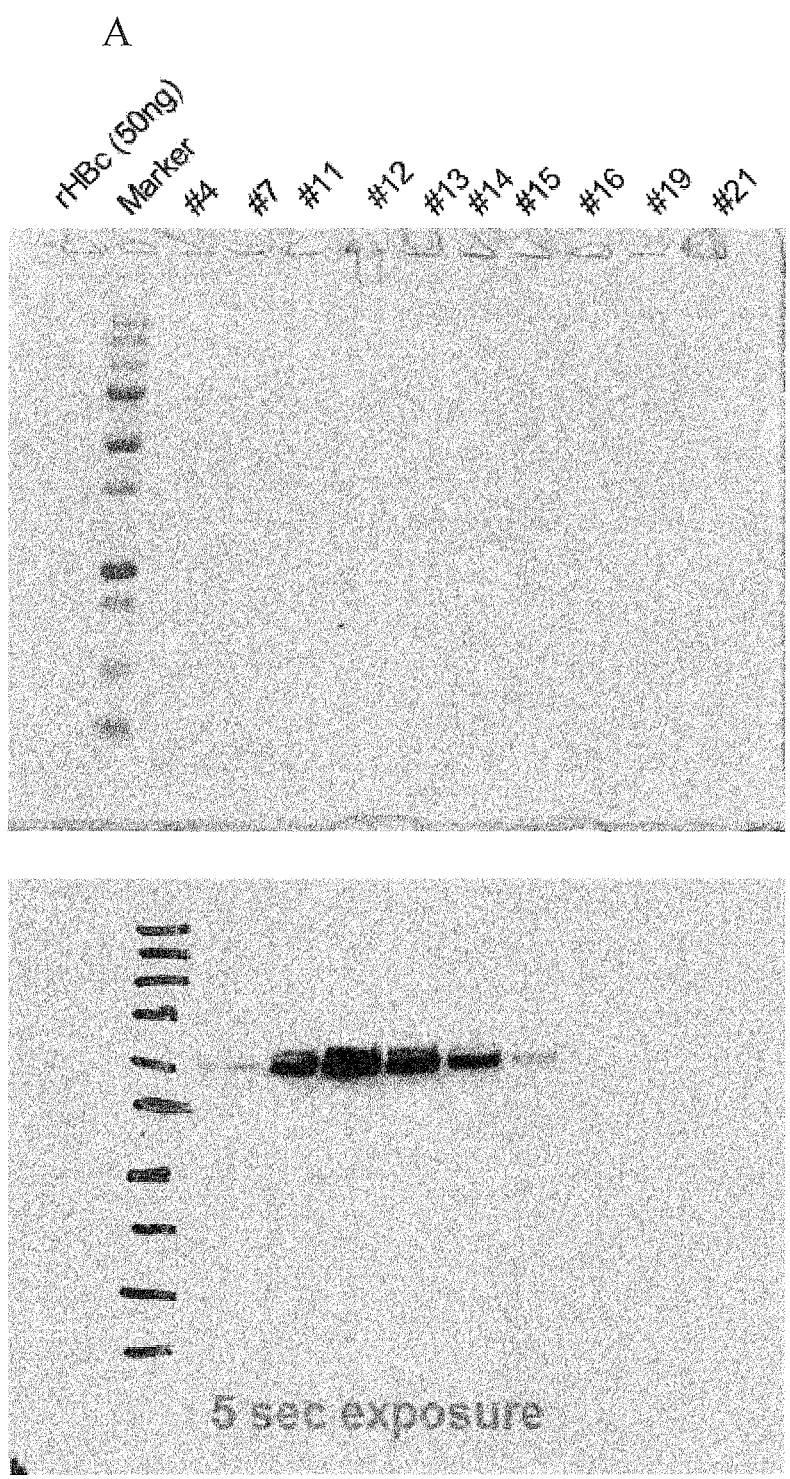
FIG. 3: The CL4B void was then passed over an S1000 column and the VLP isolated from fractions 12-15. Purity was confirmed by SDS-PAGE and western blot. The numbers are the tandem core positive fractions collected from the second S1000 column.
Figure 3:
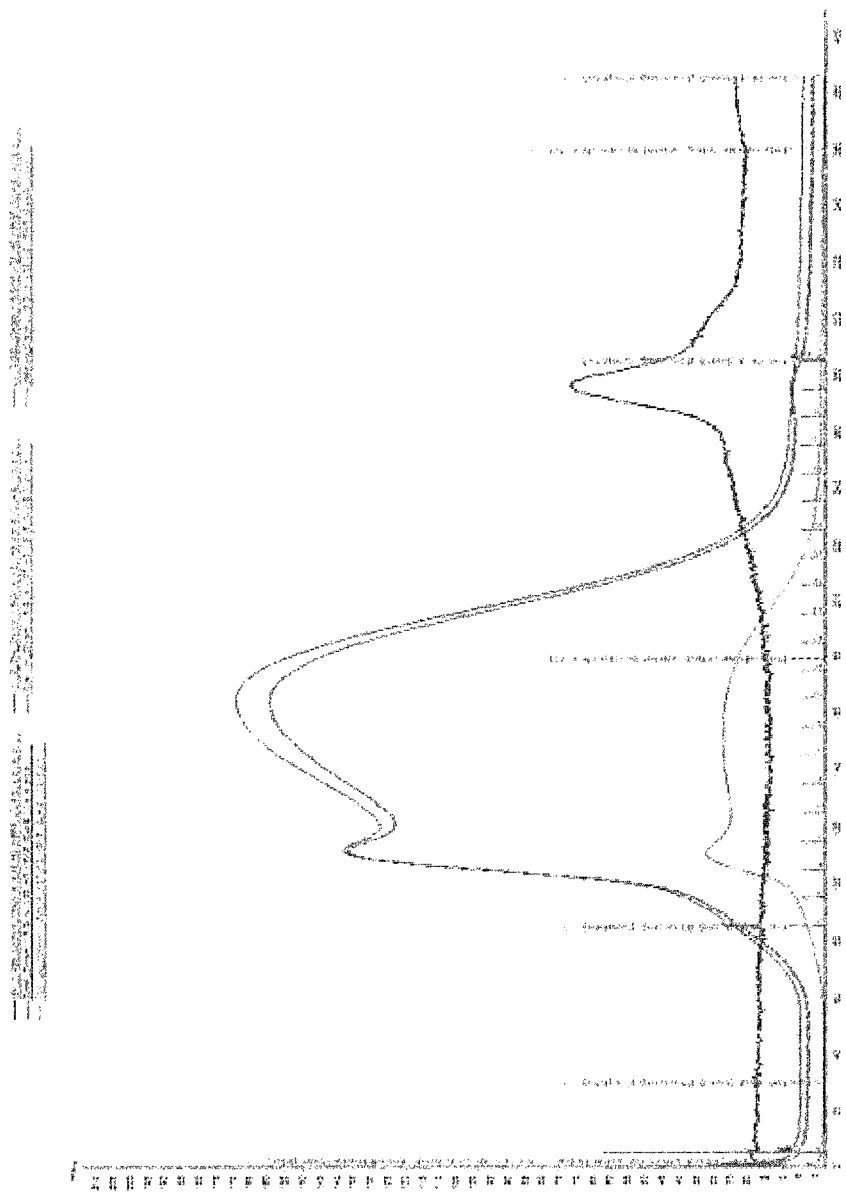

FIGS. 1 to 3 contain data for protein isolation from yeast samples. SDS-PAGE confirmed that tandem cores were found in the soluble fraction of the yeast lysate (FIG. 1). FIG. 2 shows VLP were isolated from the void volume of the CL4B column (large peak on left panel of FIG. 2B). The CL4B void was then passed over an S1000 column and the VLP isolated from fractions 12-15. Purity was confirmed by SDS-PAGE and western blot (FIG. 3).

Protein Isolation from *Baculovirus* Samples

Figure 4:
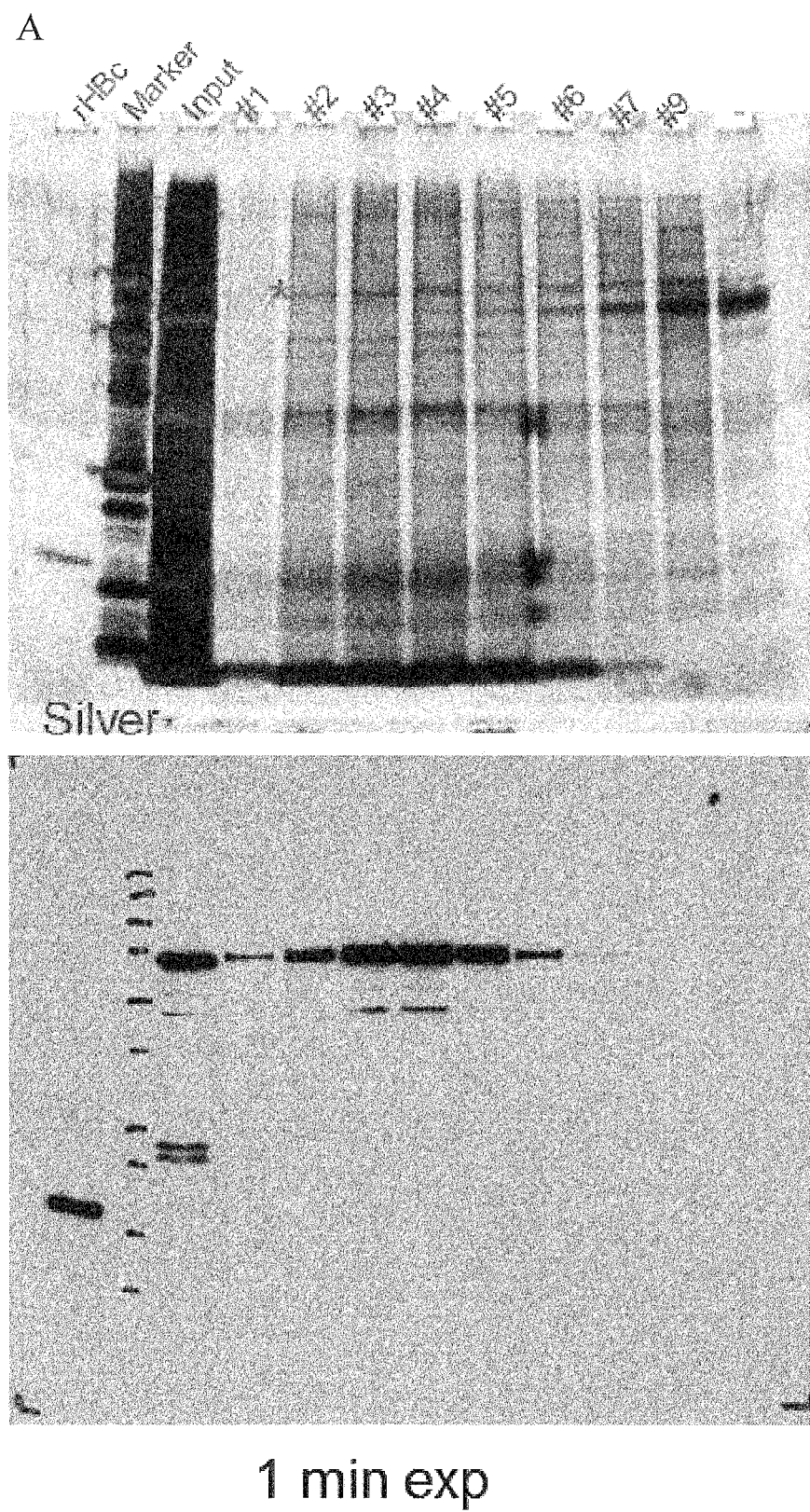
FIG. 4: (A) SDS-PAGE with silver staining confirmed that tandem core was present (marked *), but purity was not as high as in an equivalent yeast preparation. (B) Electron microscopy identified the major contaminant as baculovirion itself.
Figure 4:
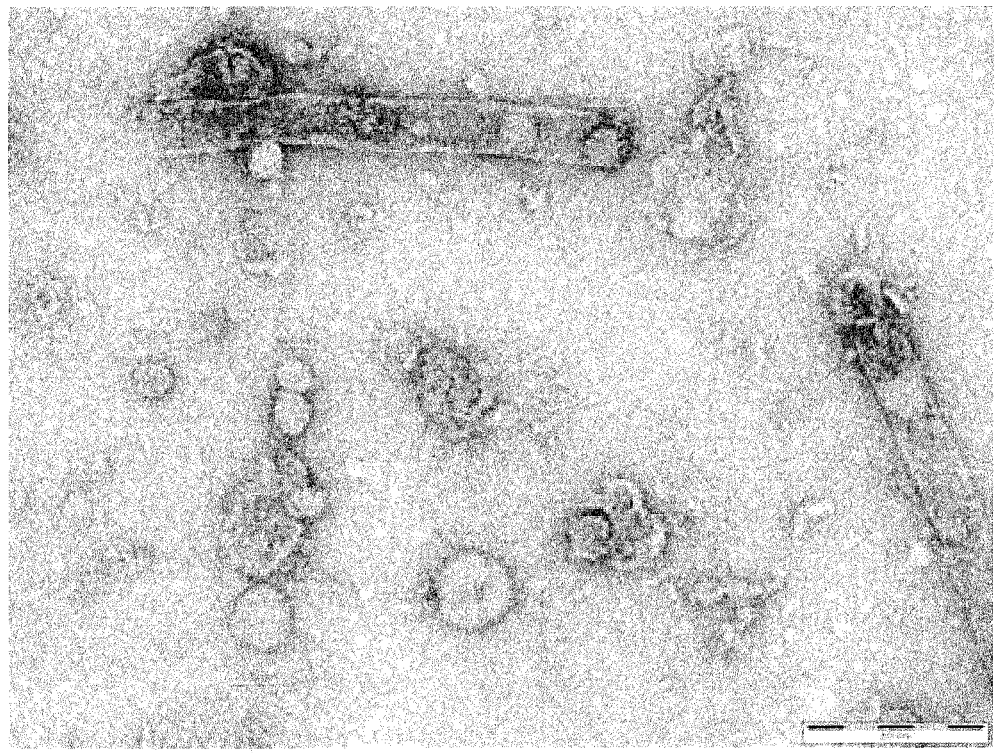

Tandem core proteins were also found in the supernatant from the initial 25,000×g spin, once again suggesting that the VLP were soluble. SDS-PAGE and western blot confirmed that very little protein was lost to the insoluble pellet. In most respects, the isolation of VLP from *baculovirus* was very similar to that from yeast. However, there was one major difference since it was common to find that baculovirion co-purified with tandem core. This was detectable both in SDS-PAGE as a 50 KDa band (FIG. 4A) and also was clearly visible as long tubules in electron micrographs (FIG. 4B).

Despite several purification iterations, it was not possible to purify the VLP made in *Baculovirus* to homogeneity. Hence, the preferred expression system for VLP is the yeast system.

Conjugation to CPS

In order to demonstrate the feasibility of the conjugation approach, Fluorescein isothiocyanate (FITC) was conjugated to VLP using the techniques outlined previously.

Figure 5:
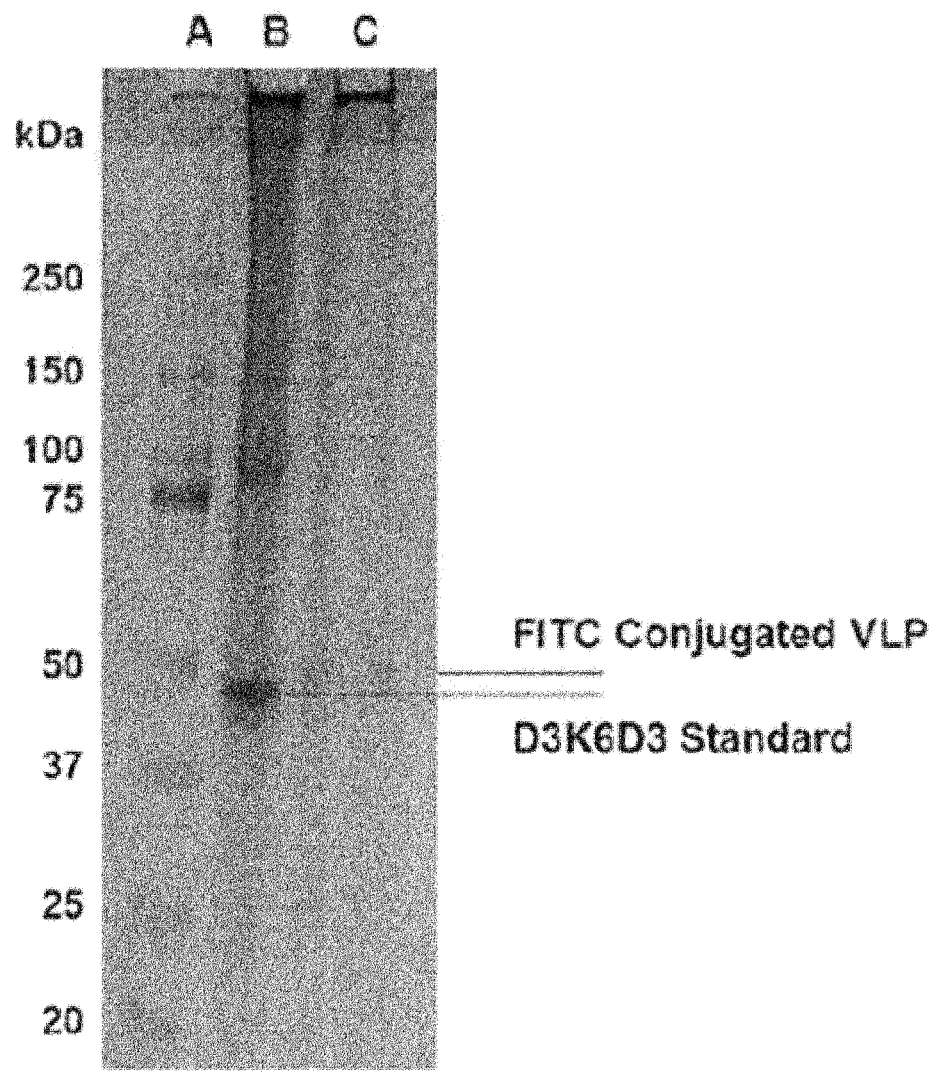
FIG. 5: Lane A: molecular weight markers, Lane B: unmodified VLP Lane C: modified VLP.
Figure 6:
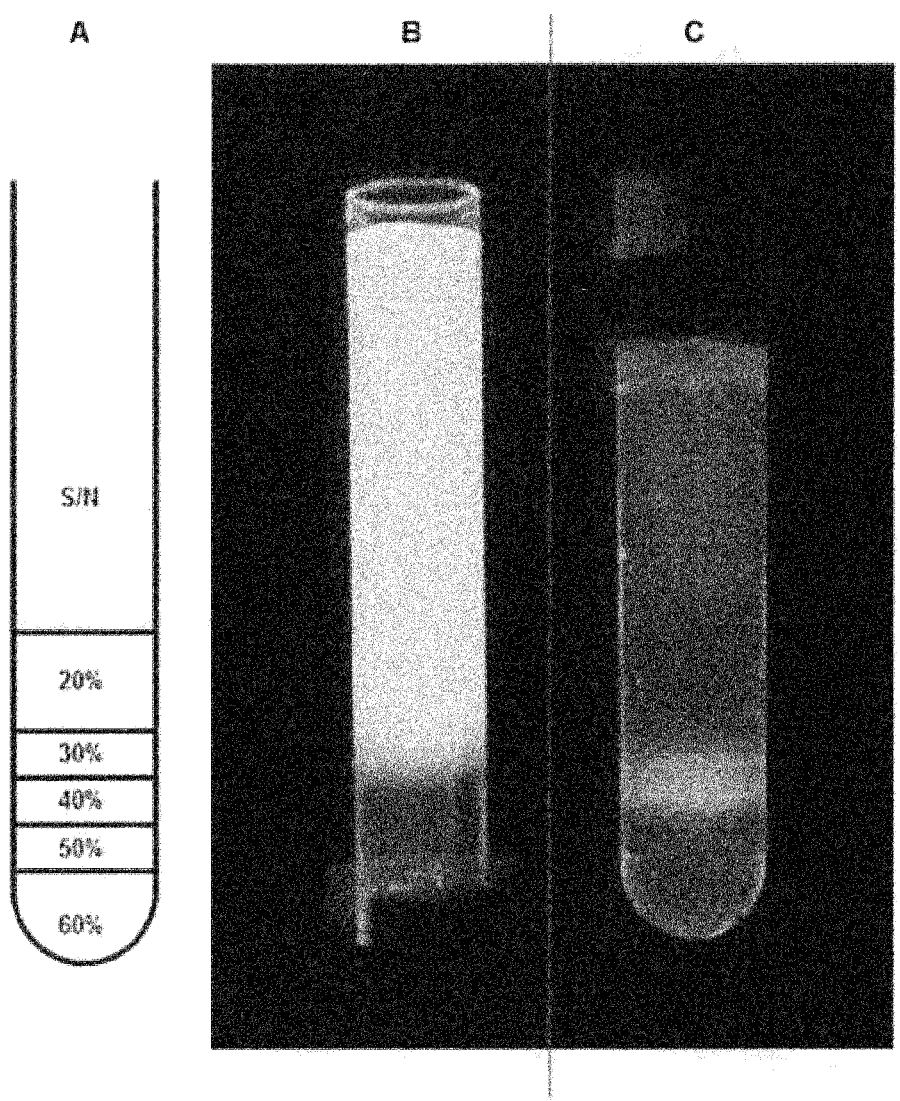
FIG. 6: (A) Schematic representation of sucrose cushion (not to scale), (B) unbound FITC and (C) FITC-VLP conjugate.

It should be noted that since SDS-PAGE is, by definition, a denaturing technique, these data show that the tandem core building block has been effectively modified since its molecular weight has increased (FIG. 5). However, when these conjugated particles were run on a sucrose cushion, a fluorescent band was seen in the VLP region thus supporting the fact that conjugation had been achieved without destruction of the VLP (FIG. 6).

Figure 7:
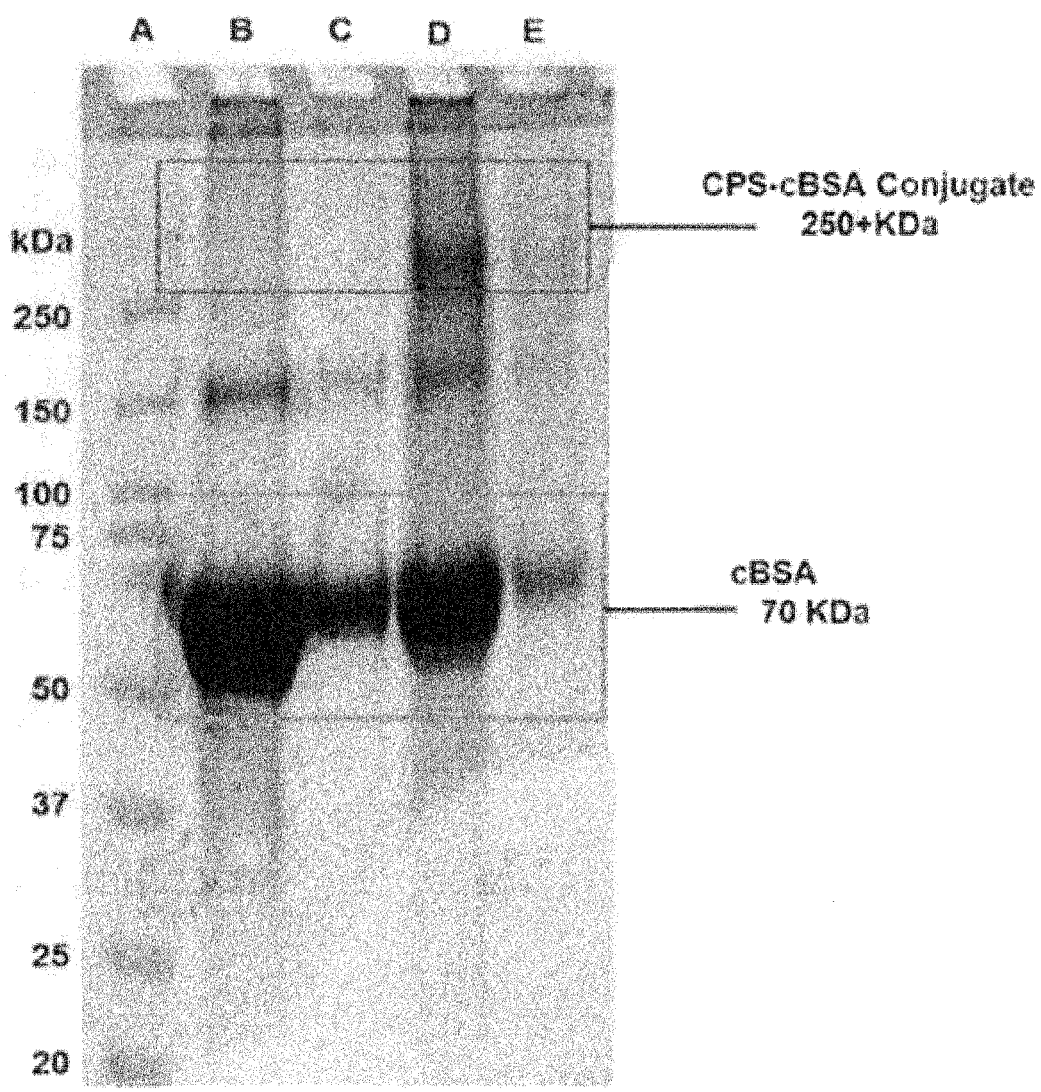
FIG. 7: Lane A: molecular weight markers, Lane B: BSA (2 mg/ml), Lane C: BSA (0.5 mg/ml), Lane D: Glycoconjugate (2 mg/ml) and Lane E: Glycoconjugate (0.5 mg/ml).

Similarly, we further demonstrate that conjugation of CPS itself is also possible by conjugating this to bovine serum albumin (FIG. 7). Thus, we have shown that conjugation of CPS is possible using our defined chemical method and that conjugation to VLP is also present. Therefore, the ligation of CPS directly to VLP should also be feasible.

Antigenicity and Immunogenicity

The conjugation of CPS to VLPs should not radically alter the glycoprotein's tertiary structure. In vivo testing of the conjugate is underway.

Figure 8:
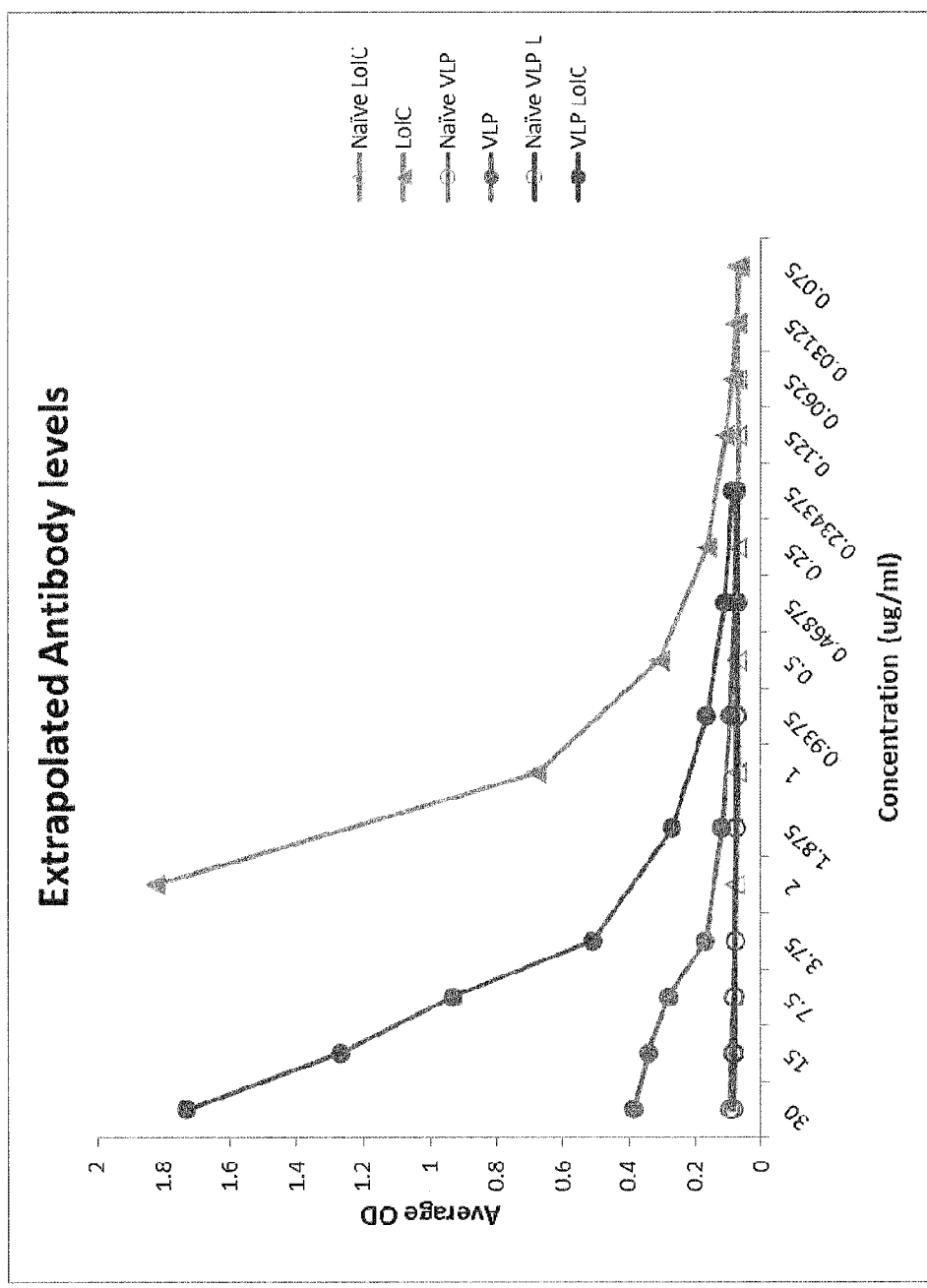
FIG. 8: VLP carrying the LolC insert were tested in an ELISA using antibodies raised in mice that had been infected with the wild-type *Burkholderia* bacterium. The line which corresponds to VLP LolC has a value for 30 ug/ml which lies between 1.6 and 1.8 average OD. The line which corresponds to unloaded VLP has a value for 30 ug/ml which lies near 0.4 average OD.

However, an alternative approach is to insert an antigen directly into the tandem core molecule. Whilst this is likely to lead to VLP which are highly decorated with the inserted antigen, it does impose potentially severe steric restrictions on the folding of the insert since it is tethered at both ends. To examine this, VLP carrying the LolC insert were tested in an ELISA using antibodies raised in mice that had been infected with the wild-type *Burkholderia* bacterium. Remarkably, the LolC carrying VLP were recognised with almost as high an affinity as wild-type Lolc protein itself. There was a small response to unloaded VLP, but the response was clearly predominantly to the insert (FIG. 8). For FIG. 8, the line which corresponds to VLP LolC has a value for 30 ug/ml which lies between 1.6 and 1.8 average OD. The line which corresponds to unloaded VLP has a value for 30 ug/ml which lies near 0.4 average OD.

Discussion

The immunogenicity of monomeric core protein is well established, as is its ability to accept antigenic inserts into its MIR. However, it is equally well documented that the technology has a major weakness because the core dimers no longer form when large or hydrophobic inserts are added, leading to a failure of VLP formation. The development of tandem core constructs overcomes this major limitation.

Whilst the utility of tandem core as a delivery system for inserted protein antigens has been demonstrated elsewhere, it is also possible to use the system in a chemical conjugation mode. In this case, non-specific linker amino acids are inserted into the MIR and disease specificity comes from the chemical conjugation of antigens to these aforementioned target amino acids. This technique further expands the antigens that tandem core can carry since glycoproteins can be conjugated which would not be possible to add using conventional cloning means. The multimeric nature of VLPs means that multiple copies of the target conjugate are added per VLP. Given that 90-120 HBc dimers are present in every VLP, very high antigen delivery densities can be reached. It is, of course, possible to combine chemical conjugation with specific antigen insertion, thus making a chimeric molecule with both a specific protein and specific glycoprotein simultaneously.

The preferred expression system for VLP is the yeast *Pichia* pastoris. However, multiple systems can be used including bacteria, *Baculovirus* and even plant based expression. These data prove that the specificity of the system comes entirely from the primary protein sequence and is not related to post-translational modifications which may be present in a particular expression system. Furthermore, we have demonstrated that the purification strategy used is applicable to any expression system and is thus likely to be scaleable to an industrial process.

The invention claimed is:

1. A protein comprising hepatitis B core antigen (HBcAg) with a sugar attached to an e1 loop.

2. The protein according to claim 1, comprising a first and a second copy of HBcAg in tandem, wherein one or both copies of HBcAg has a sugar attached to the e1 loop.

3. The protein according to claim 2, wherein the first copy has a sugar attached to the e1 loop and the second copy comprises a protein epitope in the e1 loop.

4. The protein according to claim 1, wherein the sugar or sugars are attached to lysine, arginine, asparagine, glutamine, aspartic acid or glutamic acid in the e1 loop.

5. The protein according to claim 4, wherein the e1 loop with the sugar or sugars attached comprises 1 to 12 consecutive lysines.

6. The protein according to claim 5, wherein the e1 loop with the sugar or sugars attached comprises 1 or 6 consecutive lysines.

7. The protein according to claim 4, wherein the lysine or lysines are flanked by multiple alanines.

8. The protein according to claim 1, wherein the sugar or sugars are derived from a bacterium.

9. The protein according to claim 8, wherein the bacterium is *Burkholderia*.

10. The protein according to claim 9, wherein the bacterium is *Burkholderia pseudomallei* or *Burkholderia mallei*.

11. The protein according to claim 1, wherein the sugar or sugars comprise common capsule polysaccharide (CPS).

12. The protein according to claim 1, wherein the sugar or sugars comprise an unbranched homopolymer of 1-3 linked 2-O acetyl-6-deoxy-β-D-manno-heptopyranose.

13. The protein according to claim 3, wherein the protein epitope is from *Burkholderia*.

14. The protein according to claim 3, wherein the protein epitope is from *Burkholderia pseudomallei* or *Burkholderia mallei*.

15. The protein according to claim 3, wherein the protein epitope is from LolC, PotF, OppA, Rp1, Rp2, Omp85 or Hcp2.

16. The protein according to claim 2, wherein the tandem copies of HBcAg are joined by a linker.

17. The protein according to claim 16, wherein the linker is at least 1.5 nm in length.

18. The protein according to claim 16, wherein the linker comprises multiple copies of the sequence $Gly_nSer$ $(G_nS)$ where n is from 2 to 8.

19. The protein according to claim 1, wherein the HBcAg comprises the sequence AlaAlaAlaLeuAlaAlaAla (AAALAAA; SEQ ID NO: 3).

20. A particle comprising multiple copies of a protein as claimed in claim 1.

21. A process for producing a protein as claimed in claim 1, which process comprises attaching sugar to the e1 loop.

22. The process according to claim 21, wherein the sugar is attached to the e1 loop by reductive amination.

23. The process according to claim 22, wherein the sugar is oxidised to generate a terminal aldehyde residue which is reductively aminated to primary amine in the e1 loop.

24. A pharmaceutical composition comprising a protein as claimed in claim 1 or a particle as claimed in claim 20, and a pharmaceutically acceptable carrier or diluent.

25. A method of inducing an immune response in a subject, which method comprises administering to the subject a protein as claimed in claim 1 or a particle as claimed in claim 20.

26. The method according to claim 25, for inducing an immune response against *Burkholderia*.

27. A method of vaccinating a human or animal subject, which method comprises administering to the subject a protein as claimed in claim 1 or a particle as claimed in claim 20.

28. The method according to claim 27, for vaccination against *Burkholderia*.

* * * * *

SEQUENCE LISTING

<160> NUMBER OF SEQ ID NOS: 9

<210> SEQ ID NO 1
<211> LENGTH: 639

```
<212> TYPE: DNA
<213> ORGANISM: Hepatitis B virus
<220> FEATURE:
<221> NAME/KEY: CDS
<222> LOCATION: (1)..(639)

<400> SEQUENCE: 1 atg caa ctt ttt cac ctc tgc cta atc atc tct tgt tca tgt cct act    48
Met Gln Leu Phe His Leu Cys Leu Ile Ile Ser Cys Ser Cys Pro Thr
1               5                   10                  15 gtt caa gcc tcc aag ctg tgc ctt ggg tgg ctt tgg ggc atg gac atc    96
Val Gln Ala Ser Lys Leu Cys Leu Gly Trp Leu Trp Gly Met Asp Ile
            20                  25                  30 gac cct tat aaa gaa ttt gga gct act gtg gag tta ctc tcg ttt ttg    144
Asp Pro Tyr Lys Glu Phe Gly Ala Thr Val Glu Leu Leu Ser Phe Leu
        35                  40                  45 cct tct gac ttc ttt cct tca gta cga gat ctt cta gat acc gcc tca    192
Pro Ser Asp Phe Phe Pro Ser Val Arg Asp Leu Leu Asp Thr Ala Ser
    50                  55                  60 gct ctg tat cgg gaa gcc tta gag tct cct gag cat tgt tca cct cac    240
Ala Leu Tyr Arg Glu Ala Leu Glu Ser Pro Glu His Cys Ser Pro His
65                  70                  75                  80 cat act gca ctc agg caa gca att ctt tgc tgg ggg gaa cta atg act    288
His Thr Ala Leu Arg Gln Ala Ile Leu Cys Trp Gly Glu Leu Met Thr
                85                  90                  95 cta gct acc tgg gtg ggt gtt aat ttg gaa gat cca gcg tct aga gac    336
Leu Ala Thr Trp Val Gly Val Asn Leu Glu Asp Pro Ala Ser Arg Asp
            100                 105                 110 cta gta gtc agt tat gtc aac act aat atg ggc cta aag ttc agg caa    384
Leu Val Val Ser Tyr Val Asn Thr Asn Met Gly Leu Lys Phe Arg Gln
        115                 120                 125 ctc ttg tgg ttt cac att tct tgt ctc act ttt gga aga gaa aca gtt    432
Leu Leu Trp Phe His Ile Ser Cys Leu Thr Phe Gly Arg Glu Thr Val
    130                 135                 140 ata gag tat ttg gtg tct ttc gga gtg tgg att cgc act cct cca gct    480
Ile Glu Tyr Leu Val Ser Phe Gly Val Trp Ile Arg Thr Pro Pro Ala
145                 150                 155                 160 tat aga cca cca aat gcc cct atc cta tca aca ctt ccg gag act act    528
Tyr Arg Pro Pro Asn Ala Pro Ile Leu Ser Thr Leu Pro Glu Thr Thr
                165                 170                 175 gtt gtt aga cga cga ggc agg tcc cct aga aga aga act ccc tcg cct    576
Val Val Arg Arg Arg Gly Arg Ser Pro Arg Arg Arg Thr Pro Ser Pro
            180                 185                 190 cgc aga cga agg tct caa tcg ccg cgt cgc aga aga tct caa tct cgg    624
Arg Arg Arg Arg Ser Gln Ser Pro Arg Arg Arg Arg Ser Gln Ser Arg
        195                 200                 205 gaa tct caa tgt tag                                                639
Glu Ser Gln Cys
    210

<210> SEQ ID NO 2
<211> LENGTH: 212
<212> TYPE: PRT
<213> ORGANISM: Hepatitis B virus

<400> SEQUENCE: 2

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
```

```
            35                  40                  45
Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 3
<211> LENGTH: 7
<212> TYPE: PRT
<213> ORGANISM: Artificial Sequence
<220> FEATURE:
<223> OTHER INFORMATION: sequence HBcAg may comprise

<400> SEQUENCE: 3

Ala Ala Ala Leu Ala Ala Ala
 1               5

<210> SEQ ID NO 4
<211> LENGTH: 334
<212> TYPE: PRT
<213> ORGANISM: Artificial Sequence
<220> FEATURE:
<223> OTHER INFORMATION: CoHo7e construct

<400> SEQUENCE: 4

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Glu Gly Ser Ala
 65                  70                  75                  80

Gly Gly Gly Arg Asp Pro Ala Ser Arg Asp Leu Val Val Asn Tyr Val
                 85                  90                  95

Asn Thr Asn Met Gly Leu Lys Ile Arg Gln Leu Leu Trp Phe His Ile
            100                 105                 110
```

-continued

```
Ser Cys Leu Thr Phe Gly Arg Glu Thr Val Leu Glu Tyr Leu Val Ser
    115                 120                 125
Phe Gly Val Trp Ile Arg Thr Pro Pro Ala Tyr Arg Pro Pro Asn Ala
    130                 135                 140
Pro Ile Leu Ser Thr Leu Pro Glu Thr Val Val Gly Gly Ser Ser
145                 150                 155                 160
Gly Gly Ser Gly Gly Ser Gly Gly Ser Gly Gly Ser Gly
                165                 170                 175
Gly Ser Thr Met Asp Ile Asp Pro Tyr Lys Glu Phe Gly Ala Thr Val
                180                 185                 190
Glu Leu Leu Ser Phe Leu Pro Ser Asp Phe Pro Ser Val Arg Asp
    195                 200                 205
Leu Leu Asp Thr Ala Ser Ala Leu Tyr Arg Glu Ala Leu Glu Ser Pro
    210                 215                 220
Glu His Cys Ser Pro His His Thr Ala Leu Arg Gln Ala Ile Leu Cys
225                 230                 235                 240
Trp Gly Glu Leu Met Thr Leu Ala Thr Trp Val Gly Asn Asn Leu Glu
                245                 250                 255
Phe Ala Gly Ala Ser Asp Pro Ala Ser Arg Asp Leu Val Val Asn Tyr
            260                 265                 270
Val Asn Thr Asn Met Gly Leu Lys Ile Arg Gln Leu Leu Trp Phe His
        275                 280                 285
Ile Ser Cys Leu Thr Phe Gly Arg Glu Thr Val Leu Glu Tyr Leu Val
    290                 295                 300
Ser Phe Gly Val Trp Ile Arg Thr Pro Pro Ala Tyr Arg Pro Pro Asn
305                 310                 315                 320
Ala Pro Ile Leu Ser Thr Leu Pro Glu Thr Thr Val Val Leu
                325                 330
```

<210> SEQ ID NO 5
<211> LENGTH: 328
<212> TYPE: PRT
<213> ORGANISM: Artificial Sequence
<220> FEATURE:
<223> OTHER INFORMATION: H3Ho construct

<400> SEQUENCE: 5

```
Met Ser Asp Ile Asp Pro Tyr Lys Glu Phe Gly Ala Thr Val Glu Leu
1               5                   10                  15
Leu Ser Phe Leu Pro Ser Asp Phe Pro Ser Val Arg Asp Leu Leu
                20                  25                  30
Asp Thr Ala Ser Ala Leu Tyr Arg Glu Ala Leu Glu Ser Pro Glu His
            35                  40                  45
Cys Ser Pro His His Thr Ala Leu Arg Gln Ala Ile Leu Cys Trp Gly
        50                  55                  60
Glu Leu Met Thr Leu Ala Thr Trp Val Ala Ala Leu Ala Ala Ala
65                  70                  75                  80
Glu Gly Ser Asp Pro Ala Ser Arg Asp Leu Val Val Asn Tyr Val Asn
                85                  90                  95
Thr Asn Met Gly Leu Lys Ile Arg Gln Leu Leu Trp Phe His Ile Ser
            100                 105                 110
Cys Leu Thr Phe Gly Arg Glu Thr Val Leu Glu Tyr Leu Val Ser Phe
        115                 120                 125
Gly Val Trp Ile Arg Thr Pro Pro Ala Tyr Arg Pro Pro Asn Ala Pro
    130                 135                 140
```

```
Ile Leu Ser Thr Leu Pro Glu Thr Thr Val Val Gly Gly Ser Ser Gly
145                 150                 155                 160

Gly Ser Gly Gly Ser Gly Gly Ser Gly Gly Ser Thr Met Asp Ile Asp
                165                 170                 175

Pro Tyr Lys Glu Phe Gly Ala Thr Val Glu Leu Leu Ser Phe Leu Pro
            180                 185                 190

Ser Asp Phe Phe Pro Ser Val Arg Asp Leu Leu Asp Thr Ala Ser Ala
        195                 200                 205

Leu Tyr Arg Glu Ala Leu Glu Ser Pro Glu His Cys Ser Pro His His
    210                 215                 220

Thr Ala Leu Arg Gln Ala Ile Leu Cys Trp Gly Glu Leu Met Thr Leu
225                 230                 235                 240

Ala Thr Trp Val Ala Ala Leu Ala Ala Glu Ser Gly Asp Pro
                245                 250                 255

Ala Ser Arg Asp Leu Val Val Asn Tyr Val Asn Thr Asn Met Gly Leu
            260                 265                 270

Lys Ile Arg Gln Leu Leu Trp Phe His Ile Ser Cys Leu Thr Phe Gly
        275                 280                 285

Arg Glu Thr Val Leu Glu Tyr Leu Val Ser Phe Gly Val Trp Ile Arg
    290                 295                 300

Thr Pro Pro Ala Tyr Arg Pro Pro Asn Ala Pro Ile Leu Ser Thr Leu
305                 310                 315                 320

Pro Glu Thr Thr Val Val Leu Glu
                325

<210> SEQ ID NO 6
<211> LENGTH: 682
<212> TYPE: PRT
<213> ORGANISM: Artificial Sequence
<220> FEATURE:
<223> OTHER INFORMATION: LolC-empty construct

<400> SEQUENCE: 6

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Ala Ala Leu Ala Ala Ala Glu
65                  70                  75                  80

Gly Ser Ala Leu Gly Val Ala Ala Leu Ile Val Val Leu Ser Val Met
                85                  90                  95

Asn Gly Phe Gln Lys Glu Val Arg Asp Arg Met Leu Ser Val Leu Ala
            100                 105                 110

His Val Glu Ile Phe Ser Pro Thr Gly Ser Met Pro Asp Trp Gln Leu
        115                 120                 125

Thr Ala Lys Glu Ala Arg Leu Asn Arg Ser Val Ile Gly Ala Ala Pro
130                 135                 140

Tyr Val Asp Ala Gln Ala Leu Leu Thr Arg Gln Asp Ala Val Ser Gly
145                 150                 155                 160

Val Met Leu Arg Gly Val Glu Pro Ser Leu Glu Pro Gln Val Ser Asp
                165                 170                 175
```

```
Ile Gly Lys Asp Met Lys Ala Gly Ala Leu Thr Ala Leu Ala Pro Gly
            180                 185                 190
Gln Phe Gly Ile Val Leu Gly Asn Ala Leu Ala Gly Asn Leu Gly Val
        195                 200                 205
Gly Val Gly Asp Lys Val Thr Leu Val Ala Pro Glu Gly Thr Ile Thr
    210                 215                 220
Pro Ala Gly Met Met Pro Arg Leu Lys Gln Phe Thr Val Val Gly Ile
225                 230                 235                 240
Phe Glu Ser Gly His Tyr Glu Tyr Asp Ser Thr Leu Ala Met Ile Asp
                245                 250                 255
Ile Gln Asp Ala Gln Ala Leu Phe Arg Leu Pro Ala Pro Thr Gly Val
            260                 265                 270
Arg Leu Arg Leu Thr Asp Met Gln Lys Ala Pro Gln Val Ala Arg Glu
        275                 280                 285
Leu Ala His Thr Leu Ser Gly Asp Leu Tyr Ile Arg Asp Trp Thr Gln
    290                 295                 300
Gln Asn Lys Thr Trp Phe Ser Ala Val Gln Ile Glu Lys Arg Met Met
305                 310                 315                 320
Phe Ile Ile Leu Thr Leu Ile Ile Ala Val Ala Ala Phe Asn Leu Val
                325                 330                 335
Ser Ser Leu Val Met Thr Val Thr Asn Lys Gln Ala Asp Ile Ala Ile
            340                 345                 350
Leu Arg Thr Leu Gly Ala Gln Pro Gly Ser Ile Met Lys Ile Phe Val
        355                 360                 365
Val Gln Gly Val Thr Ile Gly Phe Val Gly Thr Ala Thr Gly Val Ala
    370                 375                 380
Leu Gly Cys Leu Ile Ala Trp Ser Ile Pro Trp Leu Ile Pro Met Ile
385                 390                 395                 400
Glu His Ala Phe Gly Val Gln Phe Leu Pro Pro Ser Val Tyr Phe Ile
                405                 410                 415
Ser Glu Leu Pro Ser Glu Leu Val Ala Gly Asp Val Ile Lys Ile Gly
            420                 425                 430
Val Ile Ala Gly Ser Asp Pro Ala Ser Arg Asp Leu Val Val Asn Tyr
        435                 440                 445
Val Asn Thr Asn Met Gly Leu Lys Ile Arg Gln Leu Leu Trp Phe His
    450                 455                 460
Ile Ser Cys Leu Thr Phe Gly Arg Glu Thr Val Leu Glu Tyr Leu Val
465                 470                 475                 480
Ser Phe Gly Val Trp Ile Arg Thr Pro Pro Ala Tyr Arg Pro Pro Asn
                485                 490                 495
Ala Pro Ile Leu Ser Thr Leu Pro Glu Thr Thr Val Val Gly Gly Ser
            500                 505                 510
Ser Gly Gly Ser Gly Gly Ser Gly Gly Ser Gly Gly Ser Thr Met Asp
        515                 520                 525
Ile Asp Pro Tyr Lys Glu Phe Gly Ala Thr Val Glu Leu Leu Ser Phe
    530                 535                 540
Leu Pro Ser Asp Phe Phe Pro Ser Val Arg Asp Leu Leu Asp Thr Ala
545                 550                 555                 560
Ser Ala Leu Tyr Arg Glu Ala Leu Glu Ser Pro Glu His Cys Ser Pro
                565                 570                 575
His His Thr Ala Leu Arg Gln Ala Ile Leu Cys Trp Gly Glu Leu Met
            580                 585                 590
Thr Leu Ala Thr Trp Val Ala Ala Ala Leu Ala Ala Ala Glu Ser Gly
```

595                 600                 605
Asp Pro Ala Ser Arg Asp Leu Val Val Asn Tyr Val Asn Thr Asn Met
        610                 615                 620

Gly Leu Lys Ile Arg Gln Leu Leu Trp Phe His Ile Ser Cys Leu Thr
625                 630                 635                 640

Phe Gly Arg Glu Thr Val Leu Glu Tyr Leu Val Ser Phe Gly Val Trp
                    645                 650                 655

Ile Arg Thr Pro Pro Ala Tyr Arg Pro Pro Asn Ala Pro Ile Leu Ser
                660                 665                 670

Thr Leu Pro Glu Thr Thr Val Val Leu Glu
        675                 680

<210> SEQ ID NO 7
<211> LENGTH: 698
<212> TYPE: PRT
<213> ORGANISM: Artificial Sequence
<220> FEATURE:
<223> OTHER INFORMATION: LolC-K6 construct

<400> SEQUENCE: 7

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Ala Ala Leu Ala Ala Ala Ala Glu
65                  70                  75                  80

Gly Ser Ala Leu Gly Val Ala Ala Leu Ile Val Leu Ser Val Met
                85                  90                  95

Asn Gly Phe Gln Lys Glu Val Arg Asp Arg Met Leu Ser Val Leu Ala
                100                 105                 110

His Val Glu Ile Phe Ser Pro Thr Gly Ser Met Pro Asp Trp Gln Leu
            115                 120                 125

Thr Ala Lys Glu Ala Arg Leu Asn Arg Ser Val Ile Gly Ala Ala Pro
        130                 135                 140

Tyr Val Asp Ala Gln Ala Leu Leu Thr Arg Gln Asp Ala Val Ser Gly
145                 150                 155                 160

Val Met Leu Arg Gly Val Glu Pro Ser Leu Glu Pro Gln Val Ser Asp
                165                 170                 175

Ile Gly Lys Asp Met Lys Ala Gly Ala Leu Thr Ala Leu Ala Pro Gly
                180                 185                 190

Gln Phe Gly Ile Val Leu Gly Asn Ala Leu Ala Gly Asn Leu Gly Val
            195                 200                 205

Gly Val Gly Asp Lys Val Thr Leu Val Ala Pro Glu Gly Thr Ile Thr
        210                 215                 220

Pro Ala Gly Met Met Pro Arg Leu Lys Gln Phe Thr Val Val Gly Ile
225                 230                 235                 240

Phe Glu Ser Gly His Tyr Glu Tyr Asp Ser Thr Leu Ala Met Ile Asp
                245                 250                 255

Ile Gln Asp Ala Gln Ala Leu Phe Arg Leu Pro Ala Pro Thr Gly Val
                260                 265                 270

Arg Leu Arg Leu Thr Asp Met Gln Lys Ala Pro Gln Val Ala Arg Glu

```
            275                 280                 285
Leu Ala His Thr Leu Ser Gly Asp Leu Tyr Ile Arg Asp Trp Thr Gln
290                 295                 300

Gln Asn Lys Thr Trp Phe Ser Ala Val Gln Ile Glu Lys Arg Met Met
305                 310                 315                 320

Phe Ile Ile Leu Thr Leu Ile Ile Ala Val Ala Ala Phe Asn Leu Val
                    325                 330                 335

Ser Ser Leu Val Met Thr Val Thr Asn Lys Gln Ala Asp Ile Ala Ile
                340                 345                 350

Leu Arg Thr Leu Gly Ala Gln Pro Gly Ser Ile Met Lys Ile Phe Val
            355                 360                 365

Val Gln Gly Val Thr Ile Gly Phe Val Gly Thr Ala Thr Gly Val Ala
        370                 375                 380

Leu Gly Cys Leu Ile Ala Trp Ser Ile Pro Trp Leu Ile Pro Met Ile
385                 390                 395                 400

Glu His Ala Phe Gly Val Gln Phe Leu Pro Pro Ser Val Tyr Phe Ile
                    405                 410                 415

Ser Glu Leu Pro Ser Glu Leu Val Ala Gly Asp Val Ile Lys Ile Gly
                420                 425                 430

Val Ile Ala Gly Ser Asp Pro Ala Ser Arg Asp Leu Val Val Asn Tyr
            435                 440                 445

Val Asn Thr Asn Met Gly Leu Lys Ile Arg Gln Leu Leu Trp Phe His
        450                 455                 460

Ile Ser Cys Leu Thr Phe Gly Arg Glu Thr Val Leu Glu Tyr Leu Val
465                 470                 475                 480

Ser Phe Gly Val Trp Ile Arg Thr Pro Pro Ala Tyr Arg Pro Pro Asn
                    485                 490                 495

Ala Pro Ile Leu Ser Thr Leu Pro Glu Thr Thr Val Val Gly Gly Ser
                500                 505                 510

Ser Gly Ser Gly Gly Ser Gly Ser Gly Gly Ser Thr Met Asp
            515                 520                 525

Ile Asp Pro Tyr Lys Glu Phe Gly Ala Thr Val Glu Leu Leu Ser Phe
        530                 535                 540

Leu Pro Ser Asp Phe Phe Pro Ser Val Arg Asp Leu Leu Asp Thr Ala
545                 550                 555                 560

Ser Ala Leu Tyr Arg Glu Ala Leu Glu Ser Pro Glu His Cys Ser Pro
                    565                 570                 575

His His Thr Ala Leu Arg Gln Ala Ile Leu Cys Trp Gly Glu Leu Met
                580                 585                 590

Thr Leu Ala Thr Trp Val Ala Ala Leu Ala Ala Ala Glu Ser Gly
            595                 600                 605

Gly Ser Gly Ser Lys Lys Lys Lys Lys Gly Ser Gly Ser Ser Gly
        610                 615                 620

Asp Pro Ala Ser Arg Asp Leu Val Val Asn Tyr Val Asn Thr Asn Met
625                 630                 635                 640

Gly Leu Lys Ile Arg Gln Leu Leu Trp Phe His Ile Ser Cys Leu Thr
                    645                 650                 655

Phe Gly Arg Glu Thr Val Leu Glu Tyr Leu Val Ser Phe Gly Val Trp
                660                 665                 670

Ile Arg Thr Pro Pro Ala Tyr Arg Pro Pro Asn Ala Pro Ile Leu Ser
            675                 680                 685

Thr Leu Pro Glu Thr Thr Val Val Leu Glu
        690                 695
```

<210> SEQ ID NO 8
<211> LENGTH: 698
<212> TYPE: PRT
<213> ORGANISM: Artificial Sequence
<220> FEATURE:
<223> OTHER INFORMATION: LolC-K1 construct

<400> SEQUENCE: 8

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Ala Ala Leu Ala Ala Ala Glu
65                  70                  75                  80

Gly Ser Ala Leu Gly Val Ala Ala Leu Ile Val Val Leu Ser Val Met
                85                  90                  95

Asn Gly Phe Gln Lys Glu Val Arg Asp Arg Met Leu Ser Val Leu Ala
            100                 105                 110

His Val Glu Ile Phe Ser Pro Thr Gly Ser Met Pro Asp Trp Gln Leu
        115                 120                 125

Thr Ala Lys Glu Ala Arg Leu Asn Arg Ser Val Ile Gly Ala Ala Pro
    130                 135                 140

Tyr Val Asp Ala Gln Ala Leu Leu Thr Arg Gln Asp Ala Val Ser Gly
145                 150                 155                 160

Val Met Leu Arg Gly Val Glu Pro Ser Leu Gly Pro Gln Val Ser Asp
                165                 170                 175

Ile Gly Lys Asp Met Lys Ala Gly Ala Leu Thr Ala Leu Ala Pro Gly
            180                 185                 190

Gln Phe Gly Ile Val Leu Gly Asn Ala Leu Ala Gly Asn Leu Gly Val
        195                 200                 205

Gly Val Gly Asp Lys Val Thr Leu Val Ala Pro Glu Gly Thr Ile Thr
    210                 215                 220

Pro Ala Gly Met Met Pro Arg Leu Lys Gln Phe Thr Val Val Gly Ile
225                 230                 235                 240

Phe Glu Ser Gly His Tyr Glu Tyr Asp Ser Thr Leu Ala Met Ile Asp
                245                 250                 255

Ile Gln Asp Ala Gln Ala Leu Phe Arg Leu Pro Ala Pro Thr Gly Val
            260                 265                 270

Arg Leu Arg Leu Thr Asp Met Gln Lys Ala Pro Gln Val Ala Arg Glu
        275                 280                 285

Leu Ala His Thr Leu Ser Gly Asp Leu Tyr Ile Arg Asp Trp Thr Gln
    290                 295                 300

Gln Asn Lys Thr Trp Phe Ser Ala Val Gln Ile Glu Lys Arg Met Met
305                 310                 315                 320

Phe Ile Ile Leu Thr Leu Ile Ile Ala Val Ala Ala Phe Asn Leu Val
                325                 330                 335

Ser Ser Leu Val Met Thr Val Thr Asn Lys Gln Ala Asp Ile Ala Ile
            340                 345                 350

Leu Arg Thr Leu Gly Ala Gln Pro Gly Ser Ile Met Lys Ile Phe Val
        355                 360                 365
```

-continued

Val Gln Gly Val Thr Ile Gly Phe Val Gly Thr Ala Thr Gly Val Ala
    370                 375                 380

Leu Gly Cys Leu Ile Ala Trp Ser Ile Pro Trp Leu Ile Pro Met Ile
385                 390                 395                 400

Glu His Ala Phe Gly Val Gln Phe Leu Pro Pro Ser Val Tyr Phe Ile
                405                 410                 415

Ser Glu Leu Pro Ser Glu Leu Val Ala Gly Asp Val Ile Lys Ile Gly
            420                 425                 430

Val Ile Ala Gly Ser Asp Pro Ala Ser Arg Asp Leu Val Val Asn Tyr
        435                 440                 445

Val Asn Thr Asn Met Gly Leu Lys Ile Arg Gln Leu Leu Trp Phe His
    450                 455                 460

Ile Ser Cys Leu Thr Phe Gly Arg Glu Thr Val Leu Glu Tyr Leu Val
465                 470                 475                 480

Ser Phe Gly Val Trp Ile Arg Thr Pro Pro Ala Tyr Arg Pro Pro Asn
                485                 490                 495

Ala Pro Ile Leu Ser Thr Leu Pro Glu Thr Thr Val Val Gly Gly Ser
            500                 505                 510

Ser Gly Gly Ser Gly Gly Ser Gly Gly Ser Gly Gly Ser Thr Met Asp
        515                 520                 525

Ile Asp Pro Tyr Lys Glu Phe Gly Ala Thr Val Glu Leu Leu Ser Phe
    530                 535                 540

Leu Pro Ser Asp Phe Phe Pro Ser Val Arg Asp Leu Leu Asp Thr Ala
545                 550                 555                 560

Ser Ala Leu Tyr Arg Glu Ala Leu Glu Ser Pro Glu His Cys Ser Pro
                565                 570                 575

His His Thr Ala Leu Arg Gln Ala Ile Leu Cys Trp Gly Glu Leu Met
            580                 585                 590

Thr Leu Ala Thr Trp Val Ala Ala Ala Leu Ala Ala Ala Glu Ser Gly
        595                 600                 605

Gly Ser Gly Ser Gly Gly Gly Lys Gly Gly Gly Ser Gly Ser Ser Gly
    610                 615                 620

Asp Pro Ala Ser Arg Asp Leu Val Val Asn Tyr Val Asn Thr Asn Met
625                 630                 635                 640

Gly Leu Lys Ile Arg Gln Leu Leu Trp Phe His Ile Ser Cys Leu Thr
                645                 650                 655

Phe Gly Arg Glu Thr Val Leu Glu Tyr Leu Val Ser Phe Gly Val Trp
            660                 665                 670

Ile Arg Thr Pro Pro Ala Tyr Arg Pro Pro Asn Ala Pro Ile Leu Ser
        675                 680                 685

Thr Leu Pro Glu Thr Thr Val Val Leu Glu
    690                 695

<210> SEQ ID NO 9
<211> LENGTH: 355
<212> TYPE: PRT
<213> ORGANISM: Burkholderia

<400> SEQUENCE: 9

Ala Leu Gly Val Ala Ala Leu Ile Val Val Leu Ser Val Met Asn Gly
1               5                   10                  15

Phe Gln Lys Glu Val Arg Asp Arg Met Leu Ser Val Leu Ala His Val
            20                  25                  30

Glu Ile Phe Ser Pro Thr Gly Ser Met Pro Asp Trp Gln Leu Thr Ala

```
                35                  40                  45
Lys Glu Ala Arg Leu Asn Arg Ser Val Ile Gly Ala Ala Pro Tyr Val
    50                  55                  60

Asp Ala Gln Ala Leu Leu Thr Arg Gln Asp Ala Val Ser Gly Val Met
65                  70                  75                  80

Leu Arg Gly Val Glu Pro Ser Leu Glu Pro Gln Val Ser Asp Ile Gly
                85                  90                  95

Lys Asp Met Lys Ala Gly Ala Leu Thr Ala Leu Ala Pro Gly Gln Phe
            100                 105                 110

Gly Ile Val Leu Gly Asn Ala Leu Ala Gly Asn Leu Gly Val Gly Val
            115                 120                 125

Gly Asp Lys Val Thr Leu Val Ala Pro Glu Gly Thr Ile Thr Pro Ala
    130                 135                 140

Gly Met Met Pro Arg Leu Lys Gln Phe Thr Val Val Gly Ile Phe Glu
145                 150                 155                 160

Ser Gly His Tyr Glu Tyr Asp Ser Thr Leu Ala Met Ile Asp Ile Gln
                165                 170                 175

Asp Ala Gln Ala Leu Phe Arg Leu Pro Ala Pro Thr Gly Val Arg Leu
            180                 185                 190

Arg Leu Thr Asp Met Gln Lys Ala Pro Gln Val Ala Arg Glu Leu Ala
        195                 200                 205

His Thr Leu Ser Gly Asp Leu Tyr Ile Arg Asp Trp Thr Gln Gln Asn
    210                 215                 220

Lys Thr Trp Phe Ser Ala Val Gln Ile Glu Lys Arg Met Met Phe Ile
225                 230                 235                 240

Ile Leu Thr Leu Ile Ile Ala Val Ala Ala Phe Asn Leu Val Ser Ser
                245                 250                 255

Leu Val Met Thr Val Thr Asn Lys Gln Ala Asp Ile Ala Ile Leu Arg
            260                 265                 270

Thr Leu Gly Ala Gln Pro Gly Ser Ile Met Lys Ile Phe Val Val Gln
        275                 280                 285

Gly Val Thr Ile Gly Phe Val Gly Thr Ala Thr Gly Val Ala Leu Gly
    290                 295                 300

Cys Leu Ile Ala Trp Ser Ile Pro Trp Leu Ile Pro Met Ile Glu His
305                 310                 315                 320

Ala Phe Gly Val Gln Phe Leu Pro Pro Ser Val Tyr Phe Ile Ser Glu
                325                 330                 335

Leu Pro Ser Glu Leu Val Ala Gly Asp Val Ile Lys Ile Gly Val Ile
            340                 345                 350

Ala Gly Ser
        355
```